(12) United States Patent
Labaer et al.

(10) Patent No.: US 8,178,316 B2
(45) Date of Patent: May 15, 2012

(54) EVALUATING PROTEINS

(75) Inventors: Joshua Labaer, Matfield, MA (US); Niroshan Ramachandran, Needham, MA (US); Manuel Fuentes Garcia, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 533 days.

(21) Appl. No.: 11/770,111

(22) Filed: Jun. 28, 2007

(65) Prior Publication Data

US 2008/0071071 A1  Mar. 20, 2008

Related U.S. Application Data

(60) Provisional application No. 60/806,245, filed on Jun. 29, 2006, provisional application No. 60/806,252, filed on Jun. 29, 2006, provisional application No. 60/806,253, filed on Jun. 29, 2006.

(51) Int. Cl.
    C12P 21/06 (2006.01)
    C12M 1/00 (2006.01)
    C12M 1/34 (2006.01)
    C12M 3/00 (2006.01)
    C12Q 1/68 (2006.01)
    C12P 19/34 (2006.01)
    C12N 15/00 (2006.01)
    C07K 1/00 (2006.01)

(52) U.S. Cl. ............ 435/68.1; 435/283.1; 435/287.1; 435/287.9; 435/288.3; 435/288.4; 435/6.1; 435/320.1; 530/350

(58) Field of Classification Search .................. None
     See application file for complete search history.

(56) References Cited

U.S. PATENT DOCUMENTS

| | | |
|---|---|---|
| 4,468,470 A | 8/1984 | Aalberse |
| 4,544,395 A | 10/1985 | Evans |
| 4,868,311 A | 9/1989 | Saffran et al. |
| 5,405,746 A | 4/1995 | Uhlen |
| 5,445,934 A | 8/1995 | Fodor et al. |
| 5,641,641 A | 6/1997 | Wood |
| 5,691,152 A | 11/1997 | Burton |
| 5,854,033 A | 12/1998 | Lizardi |
| 5,874,564 A | 2/1999 | Ecker et al. |
| 5,888,732 A | 3/1999 | Hartley et al. |
| 5,922,617 A | 7/1999 | Wang et al. |
| 6,124,102 A | 9/2000 | Fodor et al. |
| 6,143,557 A | 11/2000 | Hartley et al. |
| 6,225,061 B1 | 5/2001 | Becker et al. |
| 6,303,323 B1 | 10/2001 | Laskey |
| 6,346,413 B1 | 2/2002 | Fodor et al. |
| 6,406,921 B1 | 6/2002 | Wagner et al. |
| 6,420,150 B1 | 7/2002 | Guegler et al. |
| 6,511,803 B1 | 1/2003 | Church et al. |
| 6,610,482 B1 | 8/2003 | Fodor et al. |
| 6,800,453 B2 | 10/2004 | LaBaer et al. |
| 6,911,311 B2 | 6/2005 | Manfredi |
| 6,919,211 B1 | 7/2005 | Fodor et al. |
| 6,929,944 B2 | 8/2005 | Matson |
| 7,674,752 B2 | 3/2010 | He et al. |
| 2001/0018513 A1* | 8/2001 | Baker ............ 536/25.41 |
| 2001/0041349 A1 | 11/2001 | Patron |
| 2002/0172968 A1 | 11/2002 | Liu et al. |
| 2002/0182597 A1 | 12/2002 | Kuimelis et al. |
| 2002/0192673 A1 | 12/2002 | LaBaer et al. |
| 2003/0118994 A1 | 6/2003 | Blackburn et al. |
| 2003/0148335 A1 | 8/2003 | Shen et al. |
| 2003/0207467 A1 | 11/2003 | Snyder et al. |
| 2004/0022677 A1 | 2/2004 | Wohlstadter |
| 2004/0076961 A1* | 4/2004 | Lewis ................ 435/6 |
| 2004/0161748 A1 | 8/2004 | He et al. |
| 2004/0241751 A1 | 12/2004 | Wagner et al. |
| 2005/0008674 A1 | 1/2005 | Wagner et al. |
| 2005/0048580 A1 | 3/2005 | Labaer et al. |
| 2005/0260653 A1 | 11/2005 | LaBaer et al. |
| 2006/0099704 A1 | 5/2006 | Predki et al. |
| 2006/0115810 A1 | 6/2006 | Cardone et al. |
| 2006/0234229 A1 | 10/2006 | Van Beuningen et al. |
| 2008/0071071 A1 | 3/2008 | LaBaer et al. |
| 2008/0293591 A1 | 11/2008 | Taussig et al. |

FOREIGN PATENT DOCUMENTS

| | | |
|---|---|---|
| AU | 773291 B2 | 3/2002 |
| EP | 1 026 260 | 8/2000 |
| EP | 1 159 615 | 9/2000 |
| EP | 0 818 467 | 11/2000 |
| EP | 1 360 490 | 11/2003 |
| EP | 1 309 861 | 6/2006 |
| EP | 1 512 012 | 10/2006 |
| EP | 1 737 982 | 1/2007 |
| WO | WO 90/05785 | 5/1990 |

(Continued)

OTHER PUBLICATIONS

Ramachandran et al., Science, vol. 305, pp. 86-90 (2004): Supplemental Material, pp. 1-8.*
Otteman, K. M. et al., PNAS USA, vol. 94, pp. 11201-11204 (1997).*
Higuchi, A. et al., J. Membrane Science, vol. 236, pp. 147-144 (2004).*
Fang, Y. et al., Drug Discovery today, vol. 8, pp. 755-761 (2003).*
ChemicalBook, 3-Aminopropyltriethoxysilane, downloaded from www.chemicalbook.com Jan. 7, 2010.*
Potter, M.J. et al., J. Am. Chem. Soc., vol. 116, pp. 10298-10299 (1994).*
Kaiser, L. et al. PNAS USA, vol. 105, pp. 15726-15731 (2008).*
Schwarz, D. et al., Proteomics, vol. 8, pp. 3933-3946 (2008).*
Fan, Y. et al., J.Am. Chem. Soc., vol. 124, pp. 2394-2395 (2002).*

(Continued)

*Primary Examiner* — Teresa E Strzelecka

(74) *Attorney, Agent, or Firm* — Fish & Richardson P.C.

(57) ABSTRACT

The disclosure features methods that include: providing a substrate that includes (i) a nucleic acid (e.g., DNA or RNA) encoding a hybrid amino acid sequence including a test amino acid sequence and an affinity tag, and (ii) a binding agent that recognizes the affinity tag; contacting the substrate with a translation effector to thereby translate the hybrid amino acid sequence; maintaining the substrate under conditions permissive for the hybrid amino acid sequence to bind the binding agent; and removing the nucleic acid from the substrate. In one embodiment, the substrate includes a plurality of positionally-distinguishable addresses, for example, each include a different nucleic acid. The addresses can be located a regularly or irregularly spaced locations.

43 Claims, 4 Drawing Sheets

FOREIGN PATENT DOCUMENTS

| WO | WO 97/38127 | 10/1997 |
|---|---|---|
| WO | 98/21353 | 5/1998 |
| WO | WO 98/31700 | 7/1998 |
| WO | WO 99/06833 | 2/1999 |
| WO | WO 99/11777 | 3/1999 |
| WO | WO 99/12040 | 3/1999 |
| WO | WO 99/51773 | 10/1999 |
| WO | WO 00/04382 | 1/2000 |
| WO | WO 00/54046 | 9/2000 |
| WO | WO 01/05808 | 1/2001 |
| WO | WO 01/40803 | 6/2001 |
| WO | WO 01/51663 | 7/2001 |
| WO | WO 01/57198 | 8/2001 |
| WO | WO 01/68671 | 9/2001 |
| WO | WO 01/98458 | 12/2001 |
| WO | WO 01/98534 | 12/2001 |
| WO | WO02/12893 | 2/2002 |
| WO | WO 02/14860 | 2/2002 |
| WO | WO 02/18648 | 3/2002 |
| WO | WO02/059601 | 8/2002 |
| WO | WO03/012124 | 2/2003 |
| WO | 2004/011031 | 2/2004 |
| WO | 2004/034996 | 4/2004 |
| WO | WO2005/108615 | 11/2005 |

OTHER PUBLICATIONS

Braun et al., "Proteome-scale purification of human proteins from bacteria", *PNAS* 99(5):2654-2659 (2002).

Brizuela et al., "FLEXGene repository: from sequenced genomes to gene repositories for high-throughput functional biology and proteomics", *Mol. Biochem. Parasitol.* 118:155-165 (2001).

Brizuela et al., "The FLEXGene repository: exploiting the fruits of the genome projects by creating a needed resource to face the challenges of the post-genomic era", *Arch Med Res.* 33:318-324 (2002).

Cahill, E. Nordhoff, "Protein arrays and their role in proteomics," *Adv. Biochem. Eng. Biotechnol.*, 83:177 (2003).

deWildt et al., "Antibody arrays for high-throughput screening of antibody-antigen interactions", Nature Biotechnology 18:989-994 (2000).

Garcia-Parajo et al., "Real-time light-driven dynamics of the fluorescence emission in single green fluorescent protein molecules", Proc. Natl. Acad. Sci. 97:7237-7242 (2000).

Ge, "UPA, a universal protein array system for quantitative detection of protein-protein, protein-DNA, protein-RNA and protein-ligand interactions", Nucleic Acids Res. 28, e3, i-vii (2000).

Haab, M. Dunham, P. Brown, "Protein microarrays for highly parallel detection and quantitation of specific proteins and antibodies in complex solutions," *Genome* Biol. 2 (2001).

He and Taussig, "Single step generation of protein arrays from DNA by cell-free expression and in situ immobilisation (PISA method)", Nucleic Acids Res. 29, e73, 1-6 (2001). Institute of Proteomics Research Web page, www.hip.harvard.edu/research.html, printed Oct. 25, 2000.

He et al., "DiscernArray technology: a cell-free method for the generation of protein arrays from PCR DNA", *J. Immunol. Methods* 274:265-270 (2003).

Institute of Proteomics Research, webpage dated Feb. 16, 2000 [www.hip.harvard.edu/research.html].

Jona & Snyder, "Recent developments in analytical and functional protein microarrays," *Curr. Opin. Mol. Ther.* 5:271 (2003).

Lueking et al., "Protein microarrays for gene expression and antibody screening", Anal. Biochem. 270:103-111 (1999).

LaBaer & G. Marsischky, in "Proteome Analysis—Interpreting the Genome," D.W. Speicher, Ed. (Elsevier, Philadelphia, PA, 2004), pp. 287-301.

LaBaer, "Genomics, proteomics, and the new paradigm in biomedical research", *Genet Med.* 4(6):25-95 (2002).

MacBeath and Schreiber, "Printing proteins as microarrays for high-throughput function determination", Science 289:1760-1763 (2000).

Martzen et al., "A biochemical genomics approach for identifying genes by the activity of their products", Science 286:1153-1155 (1999).

Mendoza et al., "High-throughput microarray-based enzyme-linked immunosorbent assay (ELISA)", BioTechniques 27:778-788 (1999).

Nord et al., "Microbead display of proteins by cell-free expression of anchored DNA," *J. of Biotechnology*, 106(1): 1-13 (2003).

Ohuchi et al., "In vitro method for the generation of protein libraries using PCR amplification of a single DNA molecule and coupled transcription/translation", *Nucleic Acids Res.* 26(19):4339-4346 (1998).

Steel et al., "The Flow-Thru Chip: A Three-Dimensional Biochip Platform", (2000) Microarray Biochip Technology, Mark Schena (ed.), Eaton Publishing, Chapter 5, pp. 87-117.

Ross-Macdonald et al., "Large-scale analysis of the yeast genome by transposon tagging and gene disruption ", Nature 402:413-418 (1999).

Rachez et al., "A novel protein complex that interacts with the vitamin D3 receptor in a ligand-dependent manner and enhances VDR transactivation in a cell-free system", Genes Dev. 12:1787-1800 (1998).

Rachez et al., "Ligand-dependent transcription activation by nuclear receptors requires the DRIP complex", Nature 398:824-828 (1999).

Rachez and Freedman, "Mechanisms of gene regulation by vitamin D3 receptor: a network of coactivator interactions", Gene 246:9-21 (2000).

Ramachandran et al., "Self Assembling Protein Arrays," *Science* 305:86-90 (2004).

Reboul et al., C. "elegans ORFeome version 1.1: experimental verification of the genome annotation and resource for proteome-scale protein expression.," *Nature Genet.* 34:35 (2003).

Reardon et al., "Removal of psoralen monoadducts and crosslinks by human cell free extracts," *Nucl. Acid. Res.*, 19(17): 4323-4329 (1991).

Uetz et al., "A comprehensive analysis of protein-protein interactions in *Saccharomyces cerevisiae*", Nature 403:623-631 (2000).

Walhout et al., "Protein interaction mapping in *C. elegans* using proteins involved in vulval development", Science 287:116-122 (2000).

Walhout et al., "Gateway recombinational cloning: Application to the cloning of large Numbers of open reading frames or ORFeomes," *Methods Enzymol.* 328, 575 (2000).

Walter et al., "Protein arrays for gene expression and molecular interaction screening," *Curr. Opinion in Microbiology*, 3:298-302 (2000).

Zhu et al., "Analysis of yeast protein kinases using protein chips", Nature Genetics, 26:283-289 (2000).

H. Zhu et al., "Global analysis of protein activities using proteome chips." Science 293: 2101 (2001).

Epicentre Biotechnologies, website dated Jun. 24, 2009 [www.epibio.com/techapp.asp].

Office Action for Japanese Application No. 2009-000176 dated Apr. 21, 2009.

Office Action for European Application No. 02707542.3-2404 dated Feb. 8, 2008.

Office Action for Japanese Application No. 2002-559667 dated Feb. 5, 2008.

"Psorlen-PEO4-Biotin" Technical Information, [http://web.archive.org/web/20030709113426/http://www.interchim.com/interchim/bio/produits_uptima/tech_sheet/FT-UPL7784(PsoralenBiotin).pdf (2003).

Steel et al., "Microarray Biochip Technology," Chapter 2, Mark Schena (ed), Eaton Publishing, Natick, MA p. 106, 2000.

\* cited by examiner

EVALUATING PROTEINS

CROSS-REFERENCE TO RELATED APPLICATIONS

This application claims the benefit of the filing date of U.S. Provisional Application No. 60/806,245, U.S. Provisional Application No. 60/806,252, and U.S. Provisional Application No. 60/806,253, which were filed on Jun. 29, 2006. The contents of U.S. Application No. 60/806,245, U.S. Application No. 60/806,252, and U.S. Application No. 60/806,253 are incorporated by reference as part of this application.

FEDERALLY SPONSORED RESEARCH OR DEVELOPMENT

The U.S. Government may have certain rights in this invention pursuant to Grant No. CA099191/CA117374 awarded by National Cancer Institute and Contract No. HHSN266200400053 awarded by National Institute of Allergy and Infectious Diseases.

BACKGROUND

Protein array technology has facilitated the high-throughput analysis of proteins, including the large-scale characterization of numerous binding interactions and enzymatic activities. Protein arrays can be made by a variety of methods including depositing proteins onto an array surface and translating proteins on the array.

SUMMARY

In one aspect, this disclosure features a method that includes: providing a substrate that includes (i) a nucleic acid (e.g., DNA or RNA) encoding a hybrid amino acid sequence including a test amino acid sequence and an affinity tag, and (ii) a binding agent that recognizes the affinity tag; contacting the substrate with a translation effector to thereby translate the hybrid amino acid sequence; maintaining the substrate under conditions permissive for the hybrid amino acid sequence to bind the binding agent; and removing the nucleic acid from the substrate. In one embodiment, the substrate includes a plurality of positionally-distinguishable addresses, for example, each include a different nucleic acid. The addresses can be located a regularly or irregularly spaced locations.

In one embodiment, removing the nucleic acid includes digesting the nucleic acid with an enzyme, e.g., an RNase or DNase.

The nucleic acid can be attached to the substrate, e.g., non-covalently attached by a reagent whose affinity for nucleic acid varies with buffer conditions. For example, the reagent binds nucleic acid at a pH of less than 7.5, but releases nucleic acid at a pH greater than 8. An exemplary reagent is mono-amino-N-aminoethyl (MANAE).

In one aspect, the disclosure features a substrate that includes a surface that includes a surface modification with a group that selectively binds to nucleic acid, and coding nucleic acids distributed at various locations on the surface. For example, the substrate is substantially planar. In one embodiment, the surface further includes a binding agent that recognizes a tag and the coding nucleic acids encode polypeptides that include the tag. In one embodiment, the surface modification is mono-amino-N-aminoethyl (MANAE). The substrate can further include a non-protein agent that binds to the Fc region of an antibody (e.g. a boronate group, or a metal chelating group)

In another aspect, the disclosure features method that includes: providing a substrate that includes a reactive surface having a homo-functional group capable of reacting with proteins (e.g., a primary amino group, an aldehyde group, an epoxy group, or a carboxyl group); and disposing, at a plurality of positionally distinguishable locations on the reactive surface, (i) a nucleic acid encoding a hybrid amino acid sequence including a test amino acid sequence and an affinity tag, and (ii) a binding agent that recognizes the affinity tag. The binding agent reacts with the reactive surface and becomes covalently attached to the surface. The nucleic acid and the binding agent can be disposed on the substrate separately or together. The method can further include inactivating the reactive surface and contacting the substrate with a translation effector to thereby translate the hybrid amino acid sequence at each of the locations; and maintaining the substrate under conditions permissive for the hybrid amino acid sequence to bind the binding agent.

In another aspect, the disclosure features a substrate having a surface modified with a non-protein agent that binds to the Fc region of an antibody (e.g. a boronate group, a metal chelating group, or an immobilized iminodiacetic acid (IDA) chelated to a metal, e.g., IDA-copper), wherein the substrate includes a plurality of different coding nucleic acids disposed at different locations on the surface. For example the substrate is an array. The substrate can include one or more proteins that include an Fc region bound to the non-protein agent and/or one or more antibodies that include an Fc region bound to the non-protein agent.

In still another aspect, the disclosure features a substrate including a surface modified with heterofunctional groups, including at least one group that physically absorbs proteins and at least one group that can covalently attach proteins, wherein the substrate includes a plurality of different coding nucleic acids disposed at different locations on the surface. For example, at least one of the groups can promote the physical adsorption of proteins by ionic exchange, by phenyl-boronic adsorption, or by IMAC adsorption. In some embodiments, at least one of the groups is an epoxy group. In some embodiments, the surface includes epoxy and amino groups; amino and phenyl-boronic groups; or amino and IMAC groups, or combinations thereof.

In yet another aspect, the disclosure features a substrate that includes a surface modified with a non-protein agent that binds to the Fc region of an antibody, and a reagent whose affinity for nucleic acid varies with buffer conditions, wherein the substrate comprises a plurality of different coding nucleic acids disposed at different locations on the surface.

In another aspect, the disclosure features a method that includes: (a) providing the substrate having a surface modified with a non-protein agent that binds to the Fc region of an antibody (e.g. a boronate group, a metal chelating group, or an immobilized iminodiacetic acid (IDA) chelated to a metal, e.g., IDA-copper), wherein the substrate includes a plurality of different coding nucleic acids disposed at different locations on the surface; and (b) translating the nucleic acids of the substrate by contacting the substrate with a transcription effector.

In another aspect, this disclosure features a substrate that includes: (a) a metallic surface (e.g., a gold surface); and (b) an array of protein aggregates disposed on the surface. In some embodiments, the surface is substantially planar. In other embodiments, the surface is non-planar. For example, the aggregates are formed by crosslinking soluble proteins, e.g., prior to disposing the proteins on the surface, during or after disposing the proteins on the surface.

This disclosure also features a method of providing a protein array. The method includes: providing a plurality of protein samples; forming protein aggregates in each of the protein samples; and disposing the protein aggregates on a metallic surface (e.g., a gold surface), e.g., at positionally distinguishable locations on the metallic surface. In some embodiments, the samples include soluble proteins. In some embodiments, the protein aggregates are formed by addition of a crosslinker, e.g., a homo-bifunctional crosslinker or a hetero-bifunctional crosslinker. In some embodiments, the metallic surface is substantially planar.

In another aspect, the disclosure features a method that includes providing a substrate that includes (i) a nucleic acid encoding a hybrid amino acid sequence including a test amino acid sequence and an affinity tag wherein the amino acid sequence includes a transmembrane domain, and (ii) a binding agent that recognizes the affinity tag; contacting the substrate with a translation effector to thereby translate the hybrid amino acid sequence; and maintaining the substrate under conditions permissive for the hybrid amino acid sequence to bind the binding agent, thereby attaching a protein that has a transmembrane domain to the substrate. The amino acid sequence can include at least two, three, or four transmembrane domains, e.g., seven transmembrane domains.

For example, at least some of the amino acid sequence include a mammalian receptor polypeptide or a fragment thereof. For example, at least some of the amino acid sequences include cytokine or growth factor receptors or fragments thereof.

The disclosure also features a substrate that includes a plurality of positionally distinguishable locations, wherein different proteins are attached to the substrate at the different locations, at least some of the proteins including a transmembrane domain. For example, at least some of the proteins are mammalian receptor polypeptides or include fragments thereof. At least some of the proteins can include at least two transmembrane domains, three, or four transmembrane domains, e.g., seven transmembrane domains.

In some embodiments, at least some of the proteins are translated on the substrate. In some embodiments, the substrate has at least 10, 50, 100, or 500 different proteins that include a transmembrane domain attached to it and each of these proteins is at a different positionally distinguishable location.

In another aspect, the disclosure features a method for evaluating a plurality of proteins. The method includes: providing a substrate having a plurality of different proteins attached at different positionally distinguishable locations contacting each of the locations with a cell, to provide a substrate having cells contacted thereto; and evaluating each location. For example, the cells are mammalian cells, e.g., immune cells (e.g., T cells or B cells), fibroblasts, stem cells, or neuronal cells.

In some embodiments, each location includes a reagent for evaluating a cell; and the method includes detecting the reagent at each of the locations to evaluate the effect of the respective protein at each location on the cell at that location, thereby evaluating a plurality of proteins. For example, the reagent is an antibody or other specific binding protein that can bind to a secreted agent, e.g., a secreted protein such as a cytokine or growth factor, e.g., interferon gamma.

In some embodiments, the cells include a image-detectable reagent, e.g., a fluorescent protein or an environment-sensitive dye, e.g., a calcium sensitive dye.

At least some of the proteins can include a transmembrane domain.

In another aspect, the disclosure features a method for evaluating a plurality of proteins. The method includes: providing a substrate having a plurality of different proteins attached at different positionally distinguishable locations; contacting each of the locations with a cell, to provide a substrate having cells contacted thereto; and evaluating the cell at each of the locations, thereby evaluating a plurality of proteins.

In some embodiments the cells include a image-detectable reagent, e.g., a fluorescent protein, and a calcium-sensitive dye.

In some embodiments, at least some of the proteins include a transmembrane domain.

In another aspect, the disclosure features a substrate including a plurality of positionally distinguishable locations, wherein different proteins are located on the substrate at the different locations, each location includes a cell that can interact with the protein at that particular location, and each location includes a reagent evaluating the effect of the respective protein at each location on the cell at that location.

In some embodiments the cells are immune cells, e.g., T cells or B cells. In some embodiments the reagent is an antibody that can bind to a substance, e.g., interferon gamma, secreted by the cells.

In another aspect, this disclosure features a substrate that includes: (a) a surface that is modified with a poly-blocker with multiple functional groups; and (b) an array of macromolecules (e.g., nucleic acids or proteins) disposed on the surface. For example, the poly-blocker includes a polyanion, e.g., a sulfate-dextran, a carboxymethyl-dextran, an aspartic-dextran, a glutamic dextran or a combination thereof. Combinations of poly-anions can also be used, e.g., a combination of large and small molecular weight polyanions. For example, the poly-anion can be soluble at mild conditions. It is also possible to use linkers with different sources of negative charges, e.g., carboxyls or phosphates. In some embodiments, linkers with other functional groups such as aldehydes or epoxys can be used for blocking. In some embodiments, the poly-blocker is covalently bound to the surface; in others it is non-covalently bound to the surface. The poly-blocker can range in molecular weight. For example, the average molecular weight of the poly-blocker can be, e.g., between 1-10 kDa, or higher. Higher molecular weight polyblockers, e.g., polyanions, can be used with lower density of the amino groups.

The surface can be positively-charged and the poly-blocker is negatively-charged. For example, the surface is poly-lysine or poly-arginine.

The surface can be negatively-charged and the poly-blocker is positively-charged.

In some embodiments, the surface includes aldehyde groups and the poly-blocker includes amino groups, e.g., primary aminos that react with the aldehyde groups.

In some embodiments, the surface includes activated ester groups and the poly-blocker includes amino groups that react with the ester groups.

In some embodiments, the surface includes an amino moiety (e.g., primary or secondary amino group) and the poly-blocker is a sulfate-dextran, a carboxymethyl-dextran, an aspartic-dextran, a glutamic-dextran or a combination thereof.

In some embodiments, the substrate can be glass, e.g., a glass slide. The substrate can be planar or non-planar. The substrate an include invaginations or pores.

In some embodiments, the surface can include poly-lysine or poly-arginine. The surface can include aldehyde groups and the poly-blocker can include amine groups, e.g., primary amine groups, that can react with the aldehyde groups. The surface can include activated ester groups and the poly-blocker can include amine groups that can react with the ester groups.

The substrate can include other features described herein.

In another aspect, the disclosure features a method that includes: (a) providing a substrate including a surface having a plurality of addresses; (b) disposing a plurality of nucleic acids that each include a coding region at addresses on the surface; and (c) adhering a poly-blocker with multiple functional groups to the surface. Step (c) can precede step (b) or follow step (c). For example, a different nucleic acid is disposed at the different addresses. Some addresses can be duplicates of other addresses.

In some implementations each nucleic acid of the plurality includes an anchoring agent that anchors the nucleic acid to the surface.

The coding region of each nucleic acid of the plurality encodes a polypeptide that includes a first amino acid sequence and an affinity tag. Each address can include a binding agent that recognizes the affinity tag.

The method can further include translating each nucleic acid of the plurality with a transcription and a translation effector. In many embodiments, step (c) is completed before the translating.

The method can include other features described herein.

In another aspect, the disclosure features a method that includes: (a) providing a substrate including a surface having a plurality of addresses; (b) disposing a plurality of proteins at addresses on the surface; and (c) adhering a poly-blocker with multiple functional groups to the surface. Step (c) can precede step (b) or follow step (c). The poly-blocker can regulate stringency of interactions between surface proteins and interacting agents. The method can include other features described herein.

The term "protein" refers to peptides, polypeptides, and assemblies of more than one polypeptide chains (e.g., multisubunit proteins).

Protein arrays have a variety of applications. They can be used to provide a diagnosis for a subject. For example, a sample from the subject can be contacted to the array to evaluate a property of the sample. (See, e.g., US 2005-0048580). Protein arrays can be used to evaluate one or more test compounds, e.g., to identify drug candidates. (See, e.g., US 2005-0048580). Arrays can be used to examine target protein interactions with other molecules, such as drugs, antibodies, nucleic acids, lipids, or other proteins. In addition, the array can be interrogated to find substrates and cofactors for enzymes.

The methods described herein can be adapted to a variety of formats. For example, they can used to provide an arrayed collection of ligands, e.g., specific antibodies that can measure the presence and abundance of specific proteins (or other molecules). They can be used to provide an arrayed collection of any protein of interest, or sets of proteins, for example, to study protein function (e.g., an activity such as binding or catalytic activity), drug interactions, and protein-protein interactions. The arrayed proteins can be artificial variants of a particular protein (e.g., a given natural protein). The artificial variants can be produced by targeted mutagenesis or random mutagenesis. The arrayed proteins can be related by class or function, e.g., cell surface receptors, proteases, adhesion proteins, and so forth.

The methods and surfaces described herein can also be used in non-array applications, e.g., to modify other surfaces, e.g., beads, membranes, apparati and other device parts.

The methods and surfaces described herein include, in some embodiments, covalent binding of an affinity tag to an appropriately functionalized surface. For example, the affinity tag can be part of the protein encoded by a DNA and can be captured to the surface of an array by covalent attachment to an appropriate chemical compound that recognizes the tag.

The contents of all references cited herein (inclusive of patents, patent applications, and patent application publications) are hereby incorporated by reference.

DETAILED DESCRIPTION

Protein arrays can be constructed by immobilizing nucleic acids that encode target proteins onto a surface of a substrate. A translation effector is contacted to the substrate so that the nucleic acids are expressed, producing proteins that are then immobilized in situ or otherwise stably attached. Such a protein array is referred to as a nucleic acid programmable protein arrays (NAPPA). The proteins are typically expressed with a tag that can be used to capture the protein, e.g., to the array surface, or to detect it.

As further described herein, array surfaces can include various modifications, for example, to facilitate the attachment of nucleic acids and proteins. Nucleic acids can be transiently attached, e.g., until after translation, and then removed. In addition, array surfaces can be modified, e.g., with a poly-blocker, to reduce non-specific binding and other interactions with the array surface.

Homo-Functional Binding Surfaces

Figure 1:
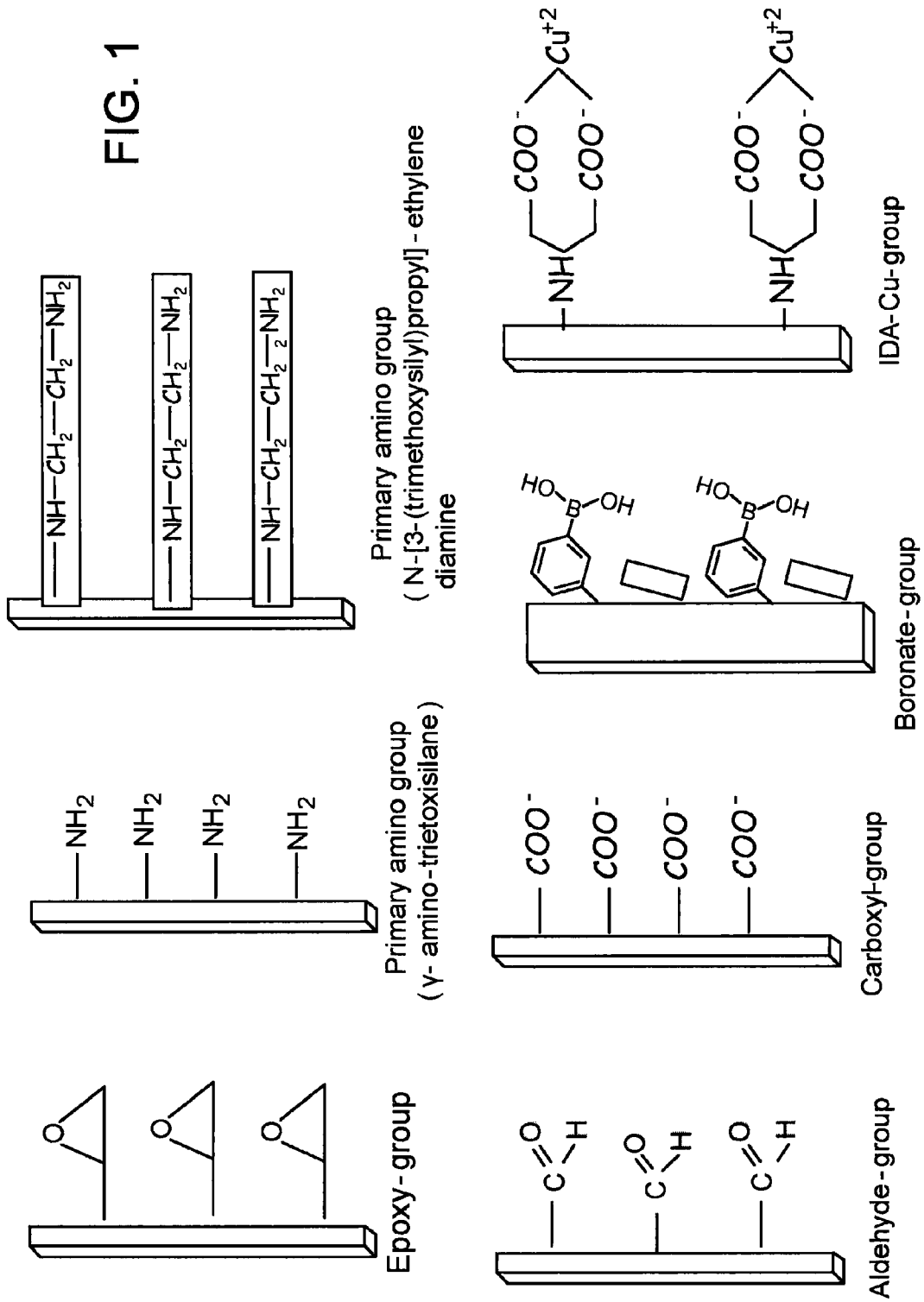
FIG. 1 is a diagram showing examples of homo-functional surface binding agents.

In one aspect, the disclosure features nucleic acid and protein arrays with surfaces modified by homo-functional surface chemistry (homo-functional binding groups) (see, e.g., FIG. 1). For example, surfaces can be activated with homo-functional groups (e.g., primary amino groups, aldehyde groups, epoxy groups, carboxyl groups) and can be used immobilize biomolecules.

Aldehyde- and epoxy-groups are stable at neutral pH values, even in wet conditions, allowing for long-term storage and/or transport before immobilization of biomolecules. In addition, substrates activated with epoxy- or aldehyde-groups can react with various common nucleophilic groups on the protein surfaces. For example, epoxy groups can react with amino, hydroxyl or thiol moieties; aldehyde groups can react with amino moieties. Such interactions can produce strong and very stable linkages (e.g., secondary amino bonds, ether bonds, thioether bonds) with minimal chemical modification of the biomolecules because, for example, pK values of the new secondary amino groups are very similar to those of the pre-existing primary ones. The epoxy groups can be used to form covalent linkage to proteins, e.g., streptavidin, antibodies, and other useful proteins, particularly binding proteins that can be attached to a NAPPA array prior to translation.

Temporary Nucleic Acid Disposal

In some implementations, it is useful to dispose nucleic acids only temporarily on an array surface. The nucleic acids can be used for a desired purpose and then removed (e.g., washed away or digested). For example, the nucleic acids can be transcribed and/or translated and then the surfaces are treated to remove the nucleic acid, e.g., DNA and RNA.

The nucleic acids can be removed by a variety of methods. Preferably, the conditions for removing the nucleic acid do not affect proteins which are immobilized to the array surface after translation.

For example, the array surface can include surface features that bind to nucleic acids under limited conditions. The conditions can be altered to remove the nucleic acids when desired. Preferably, the conditions for removing the nucleic acid do not affect protein attachment to the array surface. In one embodiment, the surface can include mono-amino-N-aminoethyl (MANAE) which binds to nucleic acid.

In one embodiment, the substrate includes ethylenediamine or a compound that has the formula $NH_2$-$[CH_2]_n$-$NH_3^+$. n is typically greater than 1, e.g., between 2 and 8, e.g., 2, 3, 4, or 5. The substrate can bind the nucleic acid using a pH-sensitive interaction. The step of washing off the nucleic acid can include altering the pH. The use of such aliphatic diamines allows for easy adsorption and/or desorption of DNA due to different pK values of the two amino groups (primary and secondary). The presence of two amino groups in a short aliphatic chain (2-6 carbons) results in decreased pK of the primary amino group. For example, at a pH between 6 and 6.5, a diamine has a double positive charge, because both primary and secondary amino groups are protonated. However, at pH 8.5, only the secondary amino group is protonated, allowing for desorption of previously adsorbed DNA. Thus, nucleic acid, absorbed to diamine at about pH 6-6.5 can be removed by increasing pH conditions to about 8.5 or greater. Changing the buffering agent in a solution is one method for altering the pH.

The array can also be treated with an agent that modifies, e.g., digests, nucleic acids, but which does not substantially affect protein. In one embodiment, the surface can be treated with DNase to remove the bound DNA. The surface can also be treated with RNase, e.g., to remove transcripts, tRNAs, and ribosomes.

The disclosure also features primary amino group substrate for nucleic acid binding, e.g., DNA binding. In one embodiment, high concentration of salt (e.g., 3-4M NaCl) can be used to wash away the nucleic acid.

Fc Domain Binding Agents

A substrate surface can also be modified to include a non-protein agent (e.g., a chemical moiety) that binds to the Fc region of an antibody. For example, the surface can include a boronate group, or a metal chelating group, e.g., immobilized iminodiacetic acid (IDA) able to chelate metals. The metal chelating group can be used immobilize copper, zinc, nickel, or other metal (e.g., any divalent metal). The surface can be used to attach a protein that includes an Fc region of an antibody or a fragment of the Fc region that interaction with such agents.

The surface can be used to attach antibodies or Fc region-containing proteins that bind to proteins that are subsequently translated on the array or can be used to attach translated proteins themselves. For example, the surface can include an antibody that recognizes an epitope tag and the nucleic acids disposed on the array surface include sequences that encode target proteins in frame with the epitope tag. In another example, the translated proteins themselves can include a region (such as an Fc region) which interacts with the surface agents, e.g., the boronate group or the metal chelating group.

Such a region can be a folded protein domain, e.g., a sequence of at least 30 amino acids. For instance the region does not include a poly-histidine tract.

Surfaces with Hetero-Functional Groups

The substrate surface can include hetero-functional (or multifunctional) groups to provide different functions to a single surface. For example, the different groups can be used to covalently bind and immobilize different biomolecules. The different groups can be used to bind and absorb and then covalently immobilize a compound.

Figure 2:
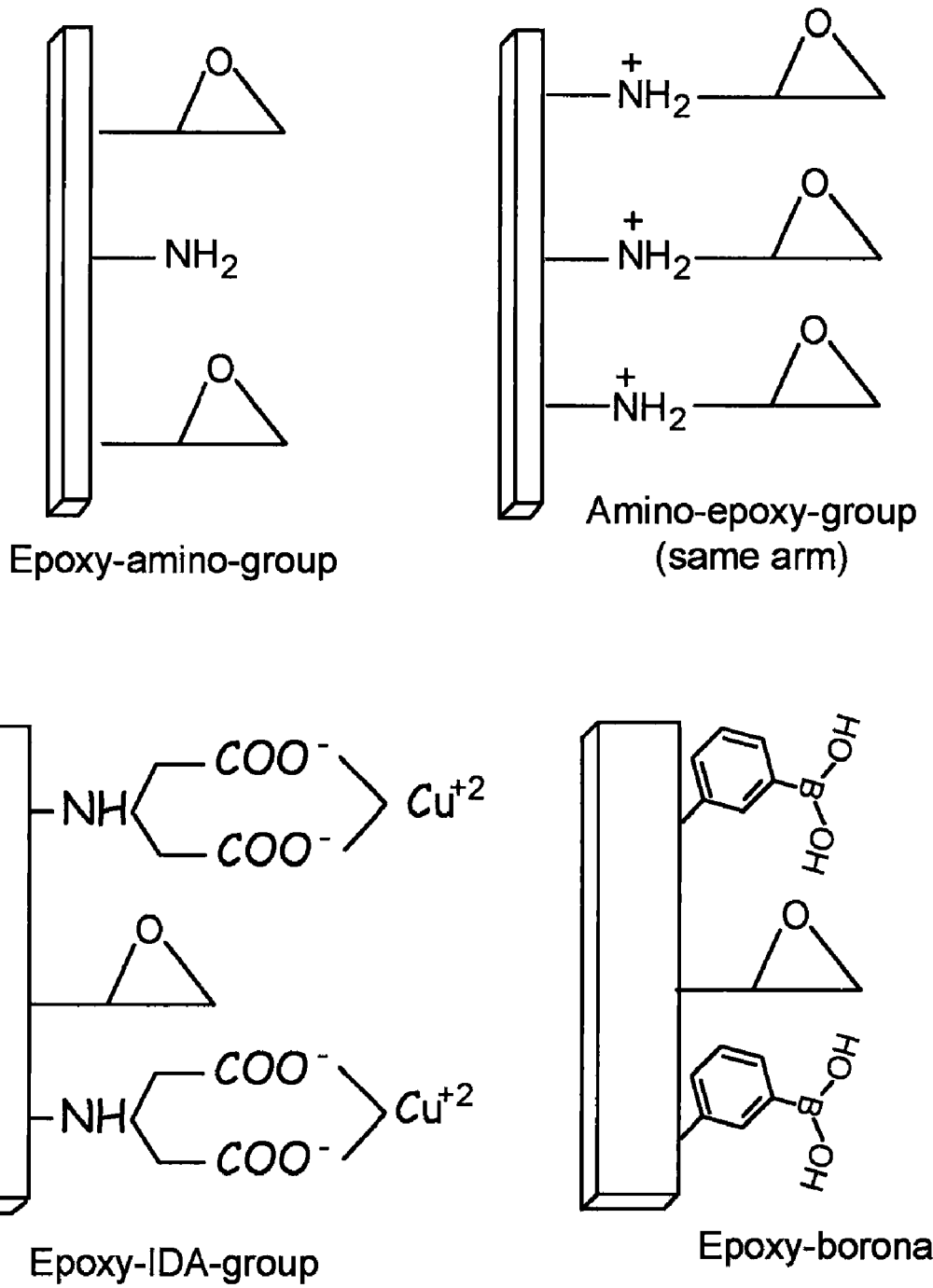
FIG. 2 is a diagram showing examples of hetero-functional surface binding agents.

For example, the multifunctional supports can include: (a) one or more functional groups that absorb proteins by non-covalent interaction (e.g., by ionic exchange (e.g., amino groups), by phenyl-boronic adsorption, or by IMAC adsorption) and (b) one or more functional groups that covalently immobilize the biomolecule (e.g., epoxy groups). FIG. 2 provides examples of hetero-functional binding agents.

Proteins can be disposed on a surface containing a hetero-functional group and maintained under conditions that permit generation of covalent linkages between nucleophilic groups of proteins (primary amino, thiol, and hydroxyl) and a layer of epoxy groups on the surface.

Another exemplary surface includes diamine and carboxyl groups. The diamine can bind a nucleic acid, e.g., DNA, and the carboxyl can immobilize an antibody that can capture a protein expressed from the nucleic acid.

The disclosure also features other useful combinations of hetero-functional groups, e.g., epoxy-amino, amino-phenyl-boronic, amino-IMAC and others. For example, one combination can be used to bind DNA and protein (i.e., DNA-binding protein, such as avidin or streptavidin that can bind to biotinylated DNA), e.g., an amine, e.g., a diamine, can preferentially bind DNA, while an epoxy group can bind a protein (with some low cross-reactivity). Another combination can be used to recruit capture antibody and DNA carrier protein and then covalently attach the protein, e.g., an amine can recruit the protein by charge close to an epoxy group to facilitate covalent binding. In another combination, a protein can be bound with an amine or epoxy and a capture antibody can be oriented with IMAC or boronate.

See generally, e.g., Mateo et al., 2003 Biomacromolecules 4:772-777; Mateo et al., 2003 Biotechnology Progress 19: 1056-1060.

Cross-Linkers

The disclosure also features bi-functional and poly-functional cross-linkers to stabilize the array reagents and increase binding capacity. Cross-linkers can increase binding capacity by allowing binding of increased number of groups and providing spacer arms. Poly-functional cross-linkers can provide stoichiometry to binding agents.

In one embodiment, the bi-functional cross-linker is a glutaraldehyde that binds primary amino groups. In another embodiment, the bi-functional cross-linker is N-(3-dimethylaminopropyl)-N'-ethylcarbodiimide HCl that can bind primary amino groups and carboxyl groups (EDCI).

Figure 3:
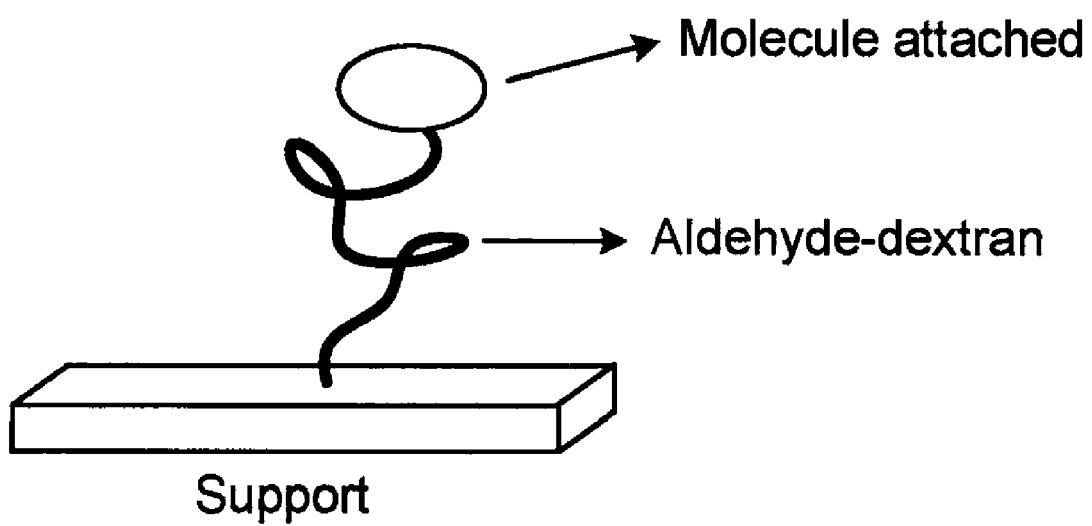
FIG. 3 is a drawing showing an example of a cross-linker used in the arrays.
Figure 4:
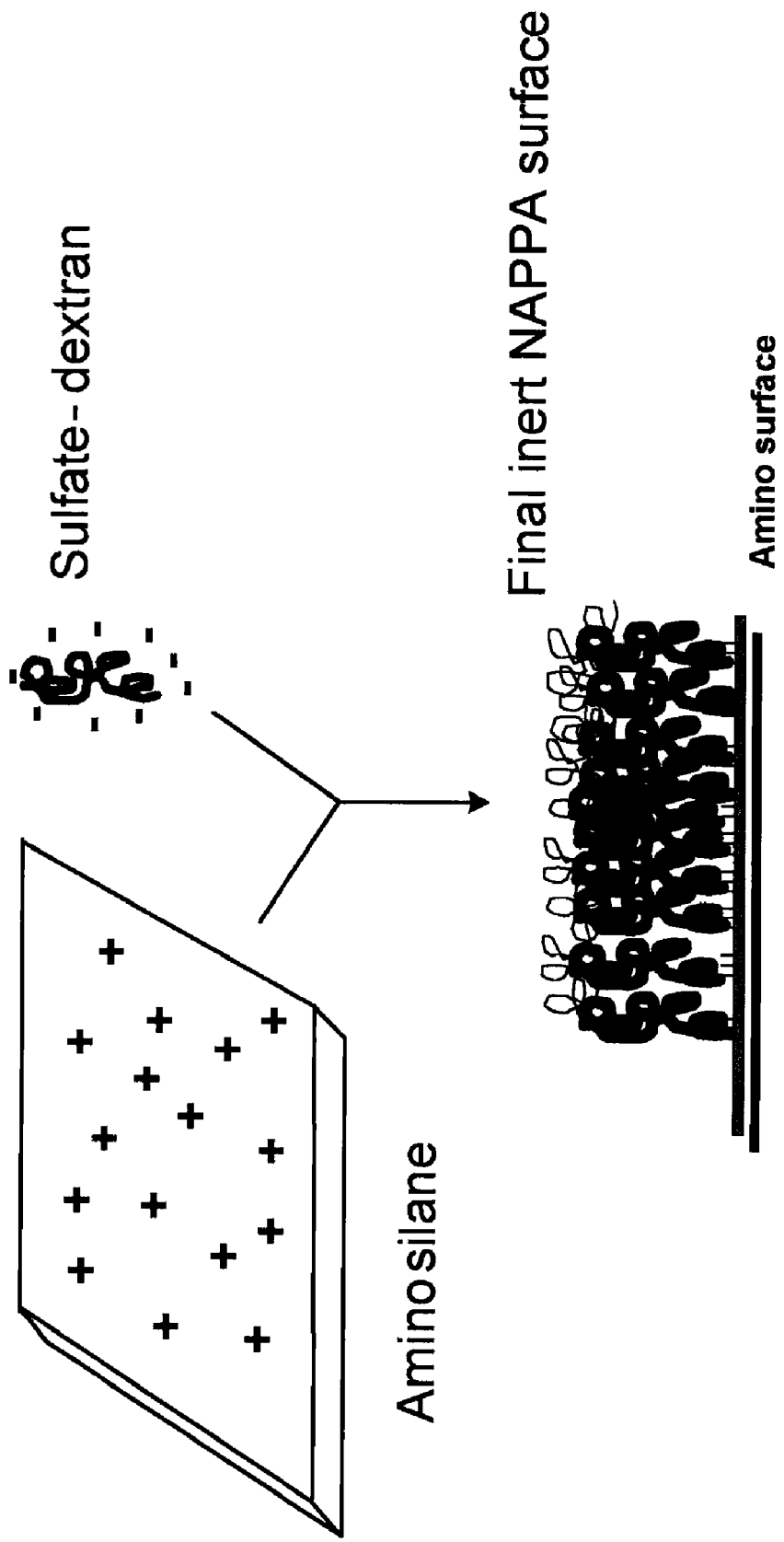
FIG. 4 is a diagram showing use of sulfate-dextran as a poly-blocker of amino silane substrate.

In one embodiment, the poly-functional cross-linker is an aldehyde-dextran that can bind primary amino groups and can be used to create aggregates of homo-functional and hetero-functional groups (see FIG. 3). Aldehyde-dextran can also be used to bind detection antibodies coupled to fluorophore (or to another detection molecule) to increase signal.

Substrates

Materials. Both solid and porous substrates are suitable for recipients for the nucleic acids and proteins described herein. In one embodiment, the substrate is a solid substrate. Potentially useful solid substrates include: glass (e.g., functionalized glass, a glass slide, porous silicate glass, a single crystal silicon, quartz, UV-transparent quartz glass), plastics and polymers (e.g., polystyrene, polypropylene, polyvinylidene difluoride, poly-tetrafluoroethylene, polycarbonate, PDMS, acrylic), metal coated substrates (e.g., gold), silicon substrates, latex, and membranes (e.g., nitrocellulose, nylon). The solid substrate can have a surface suitable for mass spectroscopy (e.g., it is a mass spectroscopy plates for MALDI), for surface plasmon resonance (SPR), or other analytical technique.

In another embodiment, the substrate is porous, e.g., a gel or matrix. Potentially useful porous substrates include: agarose gels, acrylamide gels, sintered glass, dextran, meshed polymers (e.g., macroporous crosslinked dextran, sephacryl, and sepharose), and so forth.

The substrate can include beads, e.g., beads disposed on a generally planar surface or beads in solution.

Substrate Properties. The substrate can be opaque, translucent, or transparent. The addresses can be distributed, on the substrate in one dimension, e.g., a linear array; in two dimensions, e.g., a planar array; or in three dimensions, e.g., a three dimensional array. The solid substrate may be of any convenient shape or form, e.g., square, rectangular, ovoid, or circular. In another embodiment, the solid substrate can be disc shaped and attached to a means of rotation.

In one embodiment, the substrate contains multiple addresses (positionally distinguishable locations), e.g., at least 1, 10, 100, $10^3$, $10^4$, $10^5$, $10^6$, $10^7$, $10^8$, or $10^9$ or more addresses per cm$^2$. The center to center distance can be 5 mm, 1 mm, 100 µm, 10 µm, 1 µm, 100 nm or less. The longest diameter of each address can be 5 mm, 1 mm, 100 µm, 10 µm, 1 µm, 100 nm or less. In one embodiment, each addresses contains 0 µg, 1 µg, 100 ng, 10 ng, 1 ng, 100 pg, 10 pg, 1 pg, 0.1 pg, or less of the nucleic acid or protein. In another embodiment, each address contains 100, $10^3$, $10^4$, $10^5$, $10^6$, $10^7$, $10^8$, or $10^9$ or more molecules of the nucleic acid or protein.

The substrate can include a coated surface, e.g., a metal coated surface such as a gold surface, titanium, or chromium surface. The surface can have a contact angle of between 20-70° or between 33-50° or 50-70°, e.g., about 64°. The surface may include a polymer coat (e.g., on glass or on the metal coat). The polymer can include, e.g., a reactive end, e.g., for attachment to a protein or to an anchoring agent. Exemplary termini for polymers include amines and activated esters. Exemplary polymers include alkyl chains and polyethylene glycol, and polymers that include a region, e.g., a hydrophobic and hydrophilic region, e.g., an alkyl region and a polyethylene glycol region. The substrate can include discrete regions of reactivity, e.g., a set of selective regions that include polymers with a reactive end. The regions of reactivity can be, for example, regularly spaced from one another.

Substrate Modification. The substrate can be modified to facilitate the stable attachment of linkers, capture probes, or binding agents, e.g., as described herein. Generally, a skilled artisan can use routine methods to modify a substrate in accordance with the desired application. The following are non-limiting examples of substrate modifications.

A surface can be amidated, e.g., by silylating the substrate, e.g., with trialkoxyaminosilane. Silane-treated surface can also be derivatized with homobifunctional and heterobifunctional linkers. The substrate can be derivatized, e.g., so it has a hydroxy, an amino (e.g., alkylamine), carboxyl group, N-hydroxy-succinimidyl ester, photoactivatable group, sulfhydryl, ketone, or other functional group available for reaction. The substrates can be derivatized with a mask in order to only derivatized limited areas; a chemical etch or UV light can be used to remove derivatization from selected regions.

Thus, for the preparation of glass slides, options are to derivatize the individual spots, or to derivatize the entire slide then use a physical mask, chemical etch, or UV light to cover or remove the derivatization in the areas between spots.

Partitioned Substrates. In one preferred embodiment, each address is partitioned from all other addresses in order to prevent unique molecules from diffusing to other addresses. The following are possible marcomolecules which must remain localized at the address: a template nucleic acid encoding the test amino acid sequence; amplified nucleic acid encoding the test amino acid sequence; mRNA encoding the test amino acid sequence; ribosomes, e.g., monosomes and polysomes, translating the mRNA; and the translated polypeptide. Other macromolecules that must remain localized at the address include peptides, polypeptides, and proteins.

The substrate can be partitioned, e.g., with depressions, grooves, photoresist. For example, the substrate can be a microchip with microchannels and reservoirs etched therein, e.g., by photolithography. Other non-limiting examples of substrates include multi-welled plates, e.g., 96-, 384-, 1536-, 6144-well plates, and PDMS plates. Such high-density plates are commercially available, often with specific surface treatments. Depending on the optimal volume required for each application, an appropriate density plate is selected. In another embodiment, the partitions are generated by a hydrophobic substance, e.g., a Teflon mask, grease, or a marking pen (e.g., Snowman, Japan).

In one embodiment, the substrate is designed with reservoirs isolated by protected regions, e.g., a layer of photoresist. For example, for each address, a translation effector can be isolated in one reservoir, and the nucleic acid encoding a test amino acids sequence can be isolated in another reservoir. A mask can be focused or placed on the substrate, and a photoresist barrier separating the two reservoirs can be removed by illumination. The translation effector and the nucleic acid reservoirs are mixed. The method can also include moving the substrate in order to facilitate mixing. After sufficient incubation for translation to occur, and for the nascent polypeptides to bind to a binding agent, e.g., an agent attached to the substrate, additional photoresist barriers can be removed with a second mask to facilitate washing a subset or all the addresses of the substrate, or applying a second compound to each address.

Planar Substrates. In another embodiment, the addresses are not physically partitioned, but diffusion is limited on the planar substrate, e.g., by increasing the viscosity of the solution, by providing a matrix with small pore size which excludes large macromolecules, and/or by tethering at least one of the aforementioned macromolecules. In some cases, the addresses are sufficiently separated that diffusion during the time required for translation does not result in excessive displacement of the translated polypeptide to an address other than its original address on the array. In yet another embodiment, modest or even substantial diffusion to neighboring addresses is permitted. Results, e.g., a signal of a label, are processed, e.g., using a computer system, in order to determine the position of the center of the signal. Thus, by compensating for radial diffusion, the unique address of the translated polypeptide can be accurately determined.

Non-planar substrates can also be used. For example, the non-planar substrates may include invaginations or pores.

Three-dimensional Substrates. A three-dimensional substrate can be generated, e.g., by successively applying layers of a gel matrix on a substrate. Each layer can contain a plurality of addresses. The porosity of the layers can vary, e.g., so that alternating layers have reduced porosity.

In another embodiment, a three-dimensional substrate includes stacked two-dimensional substrates, e.g., in a tower format. Each two-dimensional substrate is accessible to a dispenser and detector.

A three-dimensional substrate can include beads, e.g., beads positioned on a generally planar substrate, or beads in solution.

Gold and Other Metallic Surfaces

In some cases, it is useful to provide an array of proteins on a conductive surface, e.g., metallic surface, e.g., a gold or gold-coated surface, silver or silver-coated surface, titanium or titanium-coated surface, chromium or chromium-coated surface, and/or indium oxide or indium-oxide-coated surface. Gold-coated surfaces can be derivatized to bind proteins. In one embodiment, thiol-terminating alkanes can be used to form self-assembling monolayers on gold. Alkane linkers can be designed to contain varying lengths of carbon chains (i.e., 3 to 20) and a variety of terminating chemical moieties, e.g., amines, hydroxyls, aldehydes, nickel, activated esters and/or ethylene glycols. In one embodiment, to derivatize the surface, the linkers can be prepared in varying concentrations (e.g., 0.001 mM to 100 mM) and incubated with the surface (e.g., for 1 to 24 hours). One method of preparing proteins (thiols) on a gold surface is provided in an Example below.

To improve adherence of the proteins to the surface, it can be useful to attach aggregates of proteins to the surface rather than individual molecules to the surface, e.g., the metallic surface.

Aggregates can be formed, e.g., by crosslinking, e.g., using a homo-bifunctional or hetero-bifunctional crosslinker. Examples of such hetero-bifunctional crosslinkers include: amine-carboxyl reactive crosslinkers, amine-sulfhydryl reactive crosslinkers, sulfhydryl-hydroxyl reactive (e.g., N-[p-Maleimidophenyl]isocyanate). Examples of homo-bifunctional crosslinkers include amine or sulfydryl reactive moieties, e.g., activated esters, dextran, imidoesters, sulfosuccinimidyl suberate, and malemide. Specific examples of amine reactive cross linkers include Dimethyl adipimidate.2 HCl and Dimethyl 3,3'-dithiobispropionimidate.2 HC, and specific examples of sulfhydryl reactive crosslinkers include Bis-Maleimidoethane, Sulfosuccinimidyl 6{3'(2-pyridyldithio)-propionamido]hexanoate (SPDP), Sulfosuccinimidyl 4-(N-maleimidomethyl)cyclohexane-1-carboxylate (SMCC), and NHS-PEO$_{2-12}$-maleimide( succinimidyl-[N-maleimidopropionamido)-diethylelenglycol]ester.

The aggregates can include greater than $10^2$, $10^3$, $10^4$, or $10^5$ molecules (e.g., identical molecules or a mixture of different molecules). The aggregate can be at least 0.001, 0.01, or 0.1 nm in diameter, e.g., less than 0.2, 0.1, or 0.02 nm in diameter.

Transcription Effectors for NAPPA Applications

RNA-directed RNA polymerases and DNA-directed RNA polymerases are both suitable exemplary transcription effectors.

DNA-directed RNA polymerases include bacteriophage T7 polymerase, phage T3, phage φII, *Salmonella* phage SP6, or Pseudomonas phage gh-I, as well as archeal RNA polymerases, bacterial RNA polymerase complexes, and eukaryotic RNA polymerase complexes.

T7 polymerase is a preferred polymerase. It recognizes a specific sequence, the T7 promoter (see e.g., U.S. Pat. No. 4,952,496), which can be appropriately positioned upstream of an encoding nucleic acid sequence. Although, a DNA duplex is required for recruitment and initiation of T7 polymerase, the remainder of the template can be single stranded. In embodiments utilizing other RNA polymerases, appropriate promoters and initiations sites are selected according to the specificity of the polymerase.

RNA-directed RNA polymerases can include Qβ replicase, and RNA-dependent RNA polymerase.

Translation Effectors for NAPPA Applications

In one embodiment, the transcription/translation mix is in a minimal volume, and this volume is optimized for each application. The volume of translation effector at each address can be less than about $10^{-4}$, $10^{-5}$, $10^{-6}$, $10^{-7}$, $10^{-8}$, or $10^{-9}$ L. During dispensing and incubation, the array can be maintained in an environment to prevent evaporation, e.g., by covering the wells or by maintaining a humid atmosphere.

In another embodiment, the entire substrate can be coated or immersed in the translation effector. One possible translation effector is a translation extract prepared from cells. The translation extract can be prepared e.g., from a variety of cells, e.g., yeast, bacteria, mammalian cells (e.g., rabbit reticulocytes), plant cells (e.g., wheat germ), and archaebacteria. In a preferred embodiment, the translation extract is a wheat germ agglutinin extract or a rabbit reticulocyte lysate. In another preferred embodiment, the translation extract also includes a transcription system, e.g., a eukaryotic, prokaryotic, or viral RNA polymerase, e.g., T7 RNA polymerase. In a preferred embodiment, the translation extract is disposed on the substrate such that it can be removed by simple washing. The translation extract can be supplemented, e.g., with additional amino acids, tRNAs, tRNA synthases, and energy regenerating systems. In one embodiment, the translation extract also include an amber, ochre, or opal suppressing tRNA. The tRNA can be modified to contain an unnatural amino acid. In another embodiment, the translation extract further includes a chaperone, e.g., an agent which unfolds or folds polypeptides, (e.g., a recombinant purified chaperones, e.g., heat shock factors, GroEL/ES and related chaperones, and so forth. In another embodiment, the translation extract includes additives (e.g., glycerol, polymers, etc.) to alter the viscosity of the extract.

Affinity Tags

An amino acid sequence that encodes a member of a specific binding pair can be used as an affinity tag. The other member of the specific binding pair is attached to the substrate, either directly or indirectly. US 2005-0048580 describes various exemplary affinity tags and binding agents that can be used to attach a translated protein to the substrate.

Deposit of Nucleic Acid Sequences on Arrays

The substrate and the liquid-handling equipment are selected with consideration for required liquid volume, positional accuracy, evaporation, and cross-contamination. The density of spots can depend on the liquid volume required for a particular application, and on the substrate, e.g., how much a liquid drop spreads on the substrate due to surface tension, and the positional accuracy of the dispensing equipment.

Numerous methods are available for dispensing small volumes of liquid onto substrates. For example, U.S. Pat. No. 6,112,605 describes a device for dispensing small volumes of liquid. U.S. Pat. No. 6,110,426 describes a capillary action-based method of dispensing known volumes of a sample onto an array. The dispensed material can include a mixture described herein, e.g., a nucleic acid and a binding agent, or a nucleic acid physically associated with an attachment moiety and, optionally, a binding agent.

Nucleic acid spotted onto slides can be allowed to dry by evaporation. Dry air can be used to accelerate the process.

A nucleic acid disposed on the array can be amplified directly on the array, by a variety of methods, e.g., PCR; rolling circle amplification, isothermal RNA amplification or NASBA, and strand displacement amplification.

Nucleic Acid Sequences

Any appropriate nucleic acid, e.g., a nucleic acid for translation in a NAPPA application, can be disposed at an address of the array. The nucleic acid can be an RNA, single stranded DNA, a double stranded DNA, or combinations thereof. For example, a single-stranded DNA can include a hairpin loop at its 5' end which anneals to the T7 promoter sequence to form a duplex in that region. The nucleic acid can be an amplification products, e.g., from PCR (U.S. Pat. Nos. 4,683,196 and 4,683,202); rolling circle amplification ("RCA," U.S. Pat. No. 5,714,320), isothermal RNA amplification or NASBA (U.S. Pat. Nos. 5,130,238; 5,409,818; and 5,554,517), and strand displacement amplification (U.S. Pat. No. 5,455,166).

In one embodiment, the nucleic acid, e.g., DNA, can include a specific overhang sequence that can hybridize to complementary nucleic acid, e.g., DNA overhang sequence of, e.g., a gene sequence to be expressed. In this embodiment, a nucleic acid sequence with a specific overhang sequence is deposited at an address of the array, a mix of nucleic acid sequences that include corresponding overhangs are generated, the mix of nucleic acid sequences is added to the array, and the complementary overhangs of the added nucleic acids hybridize to the appropriate overhangs of the deposited nucleic acids.

In one embodiment, the sequence of the encoding nucleic acid is known prior to being disposed at an address. In another embodiment, the sequence of the encoding nucleic acid is unknown prior to disposal at an address. For example, the nucleic acid can be randomly obtained from a library. The nucleic acid can be sequenced after the address on which it is placed has been identified as encoding a polypeptide of interest.

A variety of schemes for depositing the coding nucleic acids are available. Exemplary methods include binding of different forms of naked DNA (supercoiled, nicked circular, linear) either by direct adsorption or by UV crosslinking to variously treated surfaces, the binding of DNA modified by the incorporation of surface reactive nucleotides, and the use of surface linking agents such as DNA binding proteins and/or hetero-bifunctional intercalating agents. Various exemplary approaches to immobilize nucleic acids can be found in Application US 2005/0260653.

As further described herein, the coding nucleic acid can be temporarily immobilized to the substrate. For example, the coding nucleic acids are deposited on the substrate, translated, and then removed after the translated protein is immobilized to the substrate.

Nucleic acids can be attached to the surface by a linker, e.g., a polymeric linker. The linker can vary in length, e.g., a population of linker molecules is used such that molecules of the nucleic acid at a particular position are attached by linkers with a variety of lengths, e.g. to generate a three-dimensional surface array. Coupling DNA to a linker can provide a variety of advantages. For example, the linker can increase ribosome access to the DNA. In some implementations, biotinylation of nucleic acids is used to distance nucleic acids away from the surface, generating a three-dimensional array.

Blocking Agents

Arrays can be used to detect specific events, e.g., specific binding interactions between a capture probe and materials in an analyte. Observations of specific events, however, are complicated by non-specific ones, for example, non-specific binding events.

Arrays can be modified by a polymer that contains multiple functional groups in close proximity. The polymer, termed "poly-blocker," is generally a non-proteinaceous polymer, yet has properties similar to a large protein. The poly-blocker is usually a homopolymer or a heteropolymer synthesized by the random addition of a set of block co-polymers. Typically the poly-blocker does not include a peptide bond, nor is a nucleic acid. In select cases in which the poly-blocker does include a peptide bond (e.g., poly-lysine or poly-arginine), the poly-blocker includes two or fewer types of amino acids or a non-programmed sequence of amino acids. Examples of poly-blockers include polyanions, such as sulfate-dextran, carboxymethyl-dextran, aspartic-dextran and polycations.

The poly-blocker can be, for example, between 1-10 kDa in molecular weight, e.g., have an average molecular weight of between 1-3, 3-5, 5-10, or 8-15 kDa. The poly-blocker can be linear or branched.

The poly-blocker can be attached to the array surface by covalent or non-covalent interactions. In some cases the surface is charged and the poly-blocker is chosen to have the opposing charge such that electrostatic forces adhere the poly-blocker to the surface.

In one embodiment, positively charged amine-coated surfaces are used. and an effective method to block these surfaces can be the use of and other poly-blockers with opposite charge to the surface charge. In another embodiment, the surface of the array can be activated with carboxyl groups, and the poly-blocker that is applied is a poly-cation, such as poly-lysine, poly-arginine, DEAE-dextran, and poly-ethylenimine (PEI).

Covalent bond formation between the poly-blocker and the surface can be used to adhere the poly-blocker to the surface. The poly-blocker and the surface are chosen to have complementary chemistry. For example, the surface includes aldehyde groups and the poly-blocker has an amino moiety (e.g., a primary amine group or a secondary amino group). In another example, the surface includes activated esters and the poly-blocker has an amino moiety.

Poly-blockers can be added at any stage of array preparation. For example, in the case of a NAPPA array, the poly-blocker can be used at one or more of the following stages:

1) before transcription and translation (pre-blocking)
2) during transcription and/or translation (e.g., to a translation extract such as a reticulocyte lysate);
3) after transcription and/or translation;
4) before or concurrent with detection (e.g., the poly-blocker can be included with a detection reagent such as a "query" antibody).

Poly-blockers can be added prior to an analyte, e.g., to block available non-specific sites on a surface prior to contacting the analyte the surface. Poly-blockers can also be used to modulate the stringency of protein-interactions. For example, the poly-blocker can be included in solution when a capture probe is contacted with an analyte.

Exemplary Applications

The nucleic acid and protein arrays described herein can be used in a number of applications. Non-limiting examples are described as follows. The regulation of cellular processes, including control of gene expression, can be investigated by examining protein-protein, protein-peptide, and protein-nucleic acid interactions; antibodies can be screened against an array of potential antigens for profiling antibody specificity or to search for common epitopes; proteins can be assayed for discrete biochemical activities; and the disruption of protein-ligand interactions by synthetic molecules or the direct detection of protein-synthetic molecule interactions can aid drug discovery. Given the versatility of array technologies, elements at each address are easily customized as appropriate for the desired application.

Nucleic acid and protein arrays can be used to characterize biomarkers and autoantibodies. For example, nucleic acids can be bound and expressed on an array surface and screened with patient serum to identify novel immunodominant antigens. A patient's immune system can produce humoral responses to antigens, these antigens may be proteins that are normally found in the body but depending on their pathophysiology there may be alterations in protein expression, mutation, degradation, or localization which may make the protein immunogenic. This can be used to evaluate subject having or suspected of having autoimmune diseases. The humoral response can also be proteins that are either pathogenic or viral in origin. Therefore by expressing potential antigens one could screen with patient sera and identify immunodominant antigens derived from tumors (breast, colorectal, prostate etc), autoimmune rheumatic diseases, pathogenic, and/or viral. The identification of immunodominant antigens with high sensitivity and specificity can be used for early detection of disease, to develop vaccines, and monitor disease progression and therapy. For some of these applications, the protein can be configured to include evaluated antigens to be used as a diagnostic tool.

Protein arrays can be used for analysis using label-free systems, such as mass spectrometry, calorimetry, and/or surface plasmon resonance. Most of these applications are implemented using substrates that have specific surface chemistry, such as surfaces with properties with suitable conductivity and ability to generate plasmons. An exemplary protein array has been adapted to the gold surface, which satisfies the demands of these label free detection systems.

The arrays can be probed with complex protein mixtures such as cell lysates, tissue, patient sera, etc. In this approach, multiple binding events may take place at each feature of the array, resulting in varying composition and amounts of bound material from feature to feature. Using label-free systems, these binding events can be measured and, in some cases, the identity, relative amounts and kinetics of the binding can be determined. This information can be used to generate patterns which can then be used to generate signatures that are specific to the sample. The ability to create unique signatures may help discern the presence of disease, biological agents, or changes in biological response.

On the other hand, nucleic acid and proteins arrays can be probed with a defined query, rather than a complex mixture. This avoids the need for labeling query molecules, such as small molecules, peptides, and nucleic acids, which may affect their binding kinetics. Using this approach, one can identify both specific and non-specific interactions with proteins on the array. For example, this approach could be applied to determine specificity of antibodies, small molecules, enzymes and receptors, as well as any off target interactions. Moreover, fragments of the binding proteins can be expressed to identify the interacting domains.

A nucleic acid or protein array can be used to detect a specific protein activity. Each address of the array is contacted with the reagents necessary for an activity assay. Then, an address having the activity is detected to thereby identify a protein having a desired activity. An activity can be detected by assaying for a product produced by a protein activity or by assaying for a substrate consumed by a protein activity.

Protein Interaction Detection

Nucleic acid and protein arrays, e.g., NAPPA arrays, can be used to detect protein-protein interactions. Moreover, the arrays can be used to generate a complete matrix of protein-protein interactions such as for a protein-interaction map (see, e.g., Walhout et al., *Science* 287: 116-122, 2000; Uetz et al., *Nature* 403, 623-631, 2000); and Schwikowski (2000) *Nature Biotech.* 18:1257). The matrix can be generated for the complete complement of a genome, proteins known or suspected to be co-regulated, proteins known or suspected to be in a regulatory network, and so forth.

In some NAPPA applications, the detection of protein-protein interactions, e.g., between a first and a second protein, entails providing at an address a nucleic acid encoding the first polypeptide and an affinity tag, and a nucleic acid encoding a second polypeptide and a recognition tag, e.g., a recognition tag described below. In one embodiment, the detection of protein-protein interactions, e.g., between a first and a second protein, entails providing at an address a nucleic acid encoding the first polypeptide and an affinity tag, and a nucleic acid encoding a second polypeptide, where the second polypeptide is detected with the use of, e.g., an antibody or a reagent specific for the second peptide.

In one NAPPA embodiment, after translation of both nucleic acids, the array is washed to remove unbound proteins and the translation effector. Detection of an address at which the second polypeptide remains bound is indicative of a protein-protein interaction between the first and second polypeptide of that address.

In another NAPPA embodiment, a third or competing polypeptide can be present during the binding step, e.g., a third encoding nucleic acid sequence lacking a tag can be included at the address.

In another embodiment, a third peptide that binds to or bridges the first and the second polypeptide can be added. The third peptide can enable the interaction of the first and the second peptides, i.e., the first and the second peptides do not interact in the absence of the third peptide.

In yet another embodiment, the stringency or conditions of the binding or washing steps are varied as appropriate to identify interactions at any range of affinity and/or specificity.

Protein-Small Molecule Screens

The arrays described herein can be used to identify a polypeptide that binds a small molecule. The small molecule can be labeled, e.g., with a fluorescent probe, and contacted to a plurality of addresses on the array (e.g., prior, during, or after translation of the programming nucleic acids). The array can be washed after maintaining the array such that the small molecule can bind to a polypeptide with an affinity tag. The signal at each address of the array can be detected to identify one or more addresses having a polypeptide that binds the small molecule.

Other signal detection methods include surface plasmon resonance (SPR) fluorescence polarization (FP), infrared spectroscopy, and nano-gravimetry. Methods for using FP are described, for example, in U.S. Pat. No. 5,800,989. Methods for using SPR are described, for example, in U.S. Pat. No. 5,641,640; and Raether (1988) *Surface Plasmons* Springer Verlag.

In another embodiment, the invention features a method of identifying a small molecule that disrupts a protein-protein interaction. The array, e.g., a NAPPA array, is programmed with a first and a second nucleic acid which respectively encode a first and second polypeptide which interact. The first polypeptide includes an affinity tag and second polypeptide includes a recognition tag. A unique small molecule is contacted to an address of the array (e.g., prior, during, or after translation of the programming nucleic acids). The array can be washed after maintaining the array such that the small molecule, the first and the second polypeptide can interact. The signal at each address of the array is detected to identify one or more addresses having a small molecule that disrupts the protein-protein interaction.

An exemplary application that exploits the ability to screen for small molecule interactions with proteins is the pre-clinical evaluation of a lead drug candidate. Drug toxicities often result not from the intended activity on the target protein, but some activity on an unrelated binding protein(s). Even when these adventitious binding proteins do not cause toxicity, they can adversely affect the drug's pharmacokinetics. A protein array can be used to identify these adventitious binders. For example, the drug candidate is contacted to a protein array that includes various potential targets, e.g., cellular proteins.

The small molecule screen could become a rapid and powerful platform by which medicinal chemistry and SAR could be performed. Chemical modifications of small molecules could be tested against the nucleic acid or protein arrays to see if changes improve specificity. Compounds could be exposed first to hepatic lysates or other metabolic extracts that mimic metabolism, in order to create potentially toxic metabolites that can also be screened for secondary targets. Recursion of this process could lead to improved specificity and tighter binding molecules.

Mass Spectroscopy

The nucleic acid and protein arrays can be used in conjunction with mass spectroscopy, e.g., to detect a modified region of the protein. An array is prepared as described herein with due consideration for the flatness, conductivity, registration and alignment, and spot density appropriate for mass spectroscopy.

In one embodiment, the method identifies a polypeptide substrate for a modifying enzyme. In a NAPPA application, each address is provided with a nucleic acid encoding a unique test polypeptide. Each address of the array is contacted with the modifying enzyme, e.g., a kinase, a methylase, a protease and so forth. The enzyme can be synthesized at the address, e.g., by including a nucleic acid encoding it at the address with the nucleic acid encoding the test sequence. After sufficient incubation to assay the modification step, each address is proteolyzed, e.g., trypsinized. The resulting peptide mixtures can be subject to MALDI-TOF mass spectroscopy analysis. The combination of peptide fragments observed at each address can be compared with the fragments expected for an unmodified protein based on the sequence of nucleic acid deposited at the same address. The use of computer programs (e.g., PAWS) to predict trypsin fragments is routine in the art. Thus, each address of the array can be analyzed by MALDI. Addresses containing modified peptide fragment relative to a predicted pattern or relative to a control array can be identified as containing potential substrates of the modifying enzyme.

The amount of modifying enzyme contacted to an address can be varied, e.g., from array to array, or from address to address.

For example, this approach can be used to identify phosphorylation by comparing the masses of peptide fragments from an address having a kinase, and an address lacking the kinase. Pandey and Mann (2000) *Nature* 405:837 describe methods of using mass spectroscopy to identify protein modification sites.

In another embodiment, in a NAPPA application, the modifying enzyme is varied at each address, and the test polypeptide, the polypeptide with the affinity tag for attachment to the substrate, is the same at each address. Both the modifying enzyme and the test polypeptide can be synthesized on the array by translation of encoding nucleic acid sequences. Mass spectroscopy is used to identify an address having a modifying enzyme with specificity for the test polypeptide as enzyme-substrate.

Mass spectroscopy can also be used to detect the binding of a second polypeptide to the target protein. In a NAPPA application, a first nucleic acid encoding a unique target amino acid sequences and an affinity tag is disposed at each address in the array. A pool of nucleic acids encoding candidate amino acid sequence is also disposed at each address of the array. Each address of the array is translated and washed to remove unbound proteins. The proteins that remain bound at each address, presumably by direct interaction with the target proteins, can then be detected and identified by mass spectroscopy.

Mass spectroscopy can be used in protein-small molecule screens, e.g., to detect binding of a test compound, e.g., a small molecule, to the target protein. In this embodiment, a first nucleic acid encoding a unique target amino acid sequences and an affinity tag is disposed at each address in the array. A pool of test compounds, e.g., small molecules, is also disposed at each address of the array. Such test compounds may or may not have to be chemically modified. Each address of the array is translated and washed to remove unbound test compounds. The test compounds that remain bound at each address, presumably by direct interaction with the target proteins, can then be detected and identified by mass spectroscopy. Small molecules are well-suited to identification by mass spectroscopy because, e.g., they fly easily in the instrument, do not require prior digestion, and can have unique signatures.

Transmembrane Proteins

Transmembrane proteins that include one or more transmembrane domains can be provided on a substrate, e.g., in an array format. The transmembrane protein is synthesized in close proximity to a substrate that includes a binding agent that immobilizes the transmembrane protein. Without being bound by theory, it is postulated that aggregation between transmembrane proteins is avoided, because the transmembrane proteins are immobilized either during translation or rapidly thereafter, e.g., before aggregation occurs.

In some exemplary implementations, a nucleic acid encoding the transmembrane protein, including at least one, two, or three transmembrane domains is deposited on the substrate. In some cases, the transmembrane protein includes four, five, six, or seven transmembrane domains, e.g., between six and twelve transmembrane domains. The nucleic acid optionally includes a sequence encoding a tag, e.g., a tag for which there is a binding agent on the substrate. The sequence encoding the tag is in frame with the sequence encoding the transmembrane protein, such that translation of the nucleic acid produces the transmembrane protein including the tag.

The substrate also includes the binding agent. Generally, the nucleic acids and the binding agent are both located in close proximity on the substrate. For example, the nucleic acid encoding the transmembrane protein can be combined with the binding agent, and the combination can be disposed on the substrate.

The substrate is then contacted with a translation effector, e.g., a translation extract such as a reticulocyte lysate. In cases where the deposited nucleic acid is DNA, the substrate can also be contacted with a transcription effector (e.g., T7 RNA polymerase). In many embodiments, the translation extract does not include lipids, micelles, or bilayer forming detergents or membranes. As a result, the transmembrane proteins are captured after translation but not inserted into membrane bilayers.

The transmembrane protein can include a full length natural protein, a natural protein without a signal sequence, or a fragment of a natural protein, e.g., a fragment that includes at least one transmembrane domain.

In one embodiment the protein includes at least five, six, or seven transmembrane domains. For example, the protein includes exactly seven transmembrane domains. The protein can be a GPCR (G-protein coupled receptor). The substrate can further include one or more nucleic acids that include regions that encode a GPCR binding protein, e.g., a G protein subunit, e.g., the α, β, and γ subunits.

The method can further include contacting the substrate with a test compound, e.g., a candidate ligand or candidate drug compound. The substrate can be evaluated to determine the interaction of the test compound with the transmembrane protein synthesized at different locations on the substrate. For example, the substrate can be evaluated to determine whether the test compound is bound to the substrate by interaction with the transmembrane protein. In another example, interaction of the test compound with the transmembrane protein is evaluated by determining whether the conformation of the transmembrane protein is altered, e.g., using a conformation specific antibody or a spectroscopic probe.

Extracellular Proteins

In one embodiment, an extracellular polypeptide or an extracellular domain can be displayed on a nucleic acid or a protein array, e.g., a NAPPA array, e.g., by contacting the array with conditions similar to the extracellular, endoplasmic reticulum, or Golgi milieu. For example, the conditions can be oxidizing or can have a redox potential that is optimized for extracellular protein production. The array can be additionally contacted with modifying enzymes found in the secretory pathway, e.g., glycosylases, proteases, and the like.

In another embodiment, in a NAPPA application, the translation effector is applied in conjunction with vesicles, e.g., endoplasmic reticular structures, and microsomes. The vesicles can include an affinity tag to anchor the vesicle to the array. In such an embodiment, the encoding nucleic acid need not contain an affinity tag.

An array of extracellular proteins or extracellular protein domains can be used to identify interactions with other extracellular proteins; or alteration of living cells (e.g., the adhesive properties, motility, or the secretory repertoire of a cell contacting the extracellular protein).

Cell-Based Assays

In another embodiment, at least one address of the array, e.g., a NAPPA after translation of encoding amino acids, is contacted with a living cell. After contacting the array, the cell or a cell parameter is monitored. For example, polypeptide growth factors can be arrayed at different addresses, and cells assayed after contact to each address. The cells can be assayed for a change in cell division, apoptosis, gene expression (e.g., by gene expression profiling), morphology changes, differentiation, proteomics analysis (e.g., by 2-D gel electrophoresis and mass spectroscopy), and specific enzymatic activities.

In one embodiment, a test protein of the array can be detached from the substrate of the array, e.g., by proteolytic cleavage at a specific protease site located between the test sequence and the tag. A released test protein can be internalized or otherwise acted upon by a cell that is contacted to the array.

In another embodiment, in a NAPPA application, the test polypeptide does not have an affinity tag, but is maintained at an address by physical separation from other addresses of the plurality. The translation effector is optionally not washed from the address. Cells are assayed after being maintained at the address as described above.

A substrate containing a plurality of different proteins can be used to evaluate cellular responses. The substrate can be contacted with cells, e.g., mammalian cells. A response of the cells can be evaluated, e.g., by imaging the substrate. For example, the cells may include a image-detectable reagent, e.g., a sensor dye (such as a calcium sensitive dye) or a reporter gene that produces a reporter proteins (e.g., a reporter protein detectable by visual imaging, e.g., luciferase or a fluorescent protein (e.g., GFP)). Generally the cells are live cells, but fixed or other non-living cells can also be used, e.g., to evaluate binding interactions.

In some embodiments, the substrate further includes a reagent for evaluating the cells. The reagent can be covalently or non-covalently bound to the substrate. For example, the reagent can be a molecule that binds to or detects a cellular component, e.g., a cell-surface protein or a protein secreted by the cells. Examples of secreted proteins include insulin, growth factors, peptide hormones, and so forth. The reagent can be an antibody or other binding protein that binds to a the cell-surface protein or the secreted protein. The substrate can be contacted with a compound. After, one or more time intervals, cells on the substrate can be evaluated. For example, the amount of the cellular component that is detected can be evaluated.

As an illustration, the substrate can be contacted with one or more compounds and evaluated to find compounds that increase or decrease secretion of a protein.

Different proteins can be evaluated a different addresses on the substrate. For example, the reagent can differ among addresses of the substrate. The different proteins can be deposited at the different addresses or can be deposited in situ.

The substrate can be an array, e.g., an array of proteins prepared by a method described herein. For example, the array can include nucleic acids, each encoding a polypeptide that includes a tag, and the array can further include a binding agent for binding to the tag, such that expressed polypeptides are anchored to the substrate by the binding agent. For example, the expressed polypeptides can be used to detect different compounds at different addresses of the array.

An example of a detection method is an enzyme-linked immunospot (ELISPOT) assay. For example, the assay can detect T-cell responses. In this example, immunological cells, e.g., T cells, are exposed to the substrate, and the cells are evaluated for a response, e.g., secretion of a particular protein, e.g., an antibody or a cytokine. The cells can be evaluated for activated T cells release factors, e.g., release of interferon gamma (IFN-γ) or interleukin-2 (IL-2).

Accordingly, in one embodiment, a substrate containing a plurality of different proteins (e.g., antigens, e.g., in full length, fragment, or peptide form) is provided. The substrate also includes a reagent (e.g., an antibody) that binds to IFN-γ or IL-2. The substrate is contacted with T cells in an appropriate medium. At one or more times after contact to the substrate, the substrate can be evaluated to determine whether there is a change in cytokine (e.g., IFN-γ or IL-2) secretion. For example, the substrate can be evaluated using a sandwich assay approach, e.g., using an antibody. For example, a secondary antibody specific for the released protein and linked to a signal molecule can also be added to visualize areas of captured proteins. The areas of captured proteins can be detected, e.g., as spots of color when visualized, around T cells. The assay can be used to detect protein release at the level of single cells.

Other examples of cells that can be contacted to an array include: bacterial cells, yeast cells, plant cells, and animal cells, particularly mammalian cells, e.g., human cells or non-human primate cells. The cells can cells from a hematopoietic lineage, e.g., hematopoietic stem cells, B cells, and T cells (including CD4+CD8− and CD4−CD8+ T cells and double positive T cells).

Diagnostic Assays

A variety of nucleic acid and protein arrays can be provided for diagnostic purposes. The array can be used as a screening tool to look for antibodies that bind to specific proteins. This could be applied for the generation of monoclonal antibodies in a high-throughput setting or in the context of measuring immune responses in a patient. ELISA techniques can be used for detection.

Antigen Arrays. One class of such arrays is an array of antigens, displayed for the purpose of determining the specificity of antibodies in a subject. The array is set up, or in case of a NAPPA array is programmed, such that each address represents a different antigen of a pathogen or of a malady (e.g., antigens significant in allergies; transplant rejection and compatibility testing; and auto-immune disorders).

In one embodiment, the array has antigens from a plurality of bacterial organisms. Computer programs can be optionally used to predict likely antigens encoded by the genome of an organism (Pizza et al. (2000) *Science* 287:1816). In a preferred embodiment, each address has disposed thereon a unique antigen. In another preferred embodiment, each address has a plurality of antigens, all being from the same species. Thus, for example, binding of a subject's antibody to an address indicates that the subject has been exposed to a pathogen represented by the address.

In another preferred embodiment, the array is used to track the progression of complex diseases. For example, diseases with antigenic variation (e.g., malaria, and trypanosomiasis) can be accurately diagnosed and/or monitored by identifying the repertoire of specific antibodies in a subject.

In another embodiment, the array can be used to detect the specific target of an autoimmune antibody. For example, isolated antibodies or serum from a subject having type I diabetes are contacted to an array having islet-cell specific proteins present at different addresses of the array.

Antigen arrays also provide a convenient means of monitoring vaccinations and disease exposure, e.g., in epidemiological studies, veterinary quarantine, and public health policy.

Antibody Arrays. Another class of diagnostic arrays is arrays of antibodies. A variety of methods are available for identifying antibodies. Monoclonal antibodies against a variety of antigens are identified. The nucleic acids encoding such antibodies are sequenced from the genome of hybridoma cells. The nucleic acid sequence is used to engineer, e.g., single-chain variants of the antibody, affibodies, ankyrin repeat proteins, and aptamers. The encoding nucleic acid sequence can be recombined into an appropriate vector In addition, the antibody sequence can be engineered to remove disulfides (Proba K (1998) *J Mol. Biol.* 275:245-53). Alternatively, e.g., in NAPPA applications, after translation and washing of the array, the array is subject to oxidizing conditions, e.g., by contacting with glutathione. The antibodies can be coupled to the array with streptococcal protein G, or *S. aureus* protein A. Further, specialized antibodies such as modified or CDR-grafted version of naturally occurring antibodies devoid of light chains can be used. The antibodies of camel (e.g., *Camelus dromedaries*) are naturally devoid of light chains (Hamers-Casterman C (1993) *Nature* 363:446-8; Desmyter et al. *Nat Struct Biol* 1996 September;3(9):803-11).

A patient sample can then be contacted to the array. Non-limiting examples of patient samples include serum proteins, proteins extracted from a biopsy, synovial fluid, cerebrospinal fluid, urine, nipple aspirate, semen, vitreous fluid etc. In addition, cells can be contacted to the array in order to query for antigens displayed on the cell surface.

In one embodiment, the sample is modified with a compound prior to being contacted to the array. For example, the sample can be biotinylated. In another embodiment, the sample is unlabelled. Arrays can be designed to identify proteins associated with various maladies, e.g., to detect antigens associated with cancer at various stages (for example, early, and pre-metastatic stages) or to provide a prediction (for example, to quantitate the abundance of an antigen correlated with a condition).

Proteins can be used as biomarkers. For example, antigens that are associated with a particular condition can be considered a biomarker. Examples of antigens include CEA, CA-125 and PSA. PSA, for example, can be used to evaluate risk or presence of prostate cancer.

In addition to detecting protein biomarkers, it is useful to evaluate a subject to detect their antibody or antibody responses. For example, the presence of an antibody can be an indicator of a disorder, e.g., an autoimmune disorder or a neoplastic disorder.

An alternative format to using an array of capture reagents is to use a reverse phase protein blot. Multiple samples can be disposed on an array. The samples can also include different fractions of an original sample, e.g., an original sample obtained form a subject. A sample can be resolved by various methods, e.g., chromatography methods or gel resolution.

Aspects of this application are further illustrated by the following examples:

EXAMPLE

Coating Amino Surface with Poly-Anions

In this example, glass slides that have primary amino groups are used. Poly-anions (for example, sulfate-dextran, carboxymethyl-dextran, aspartic-dextrans, glutamic-dextrans etc.) are used as the blocking reagent to reduce non-specific adsorption. FIG. 1 shows blocking with sulfate-dextran. Modification by poly-anions can produce a modified surface that is relatively inert, e.g., with approximately zero net charge, thereby preventing ionic adsorption.

Dextran-sulfate was prepared by sulphating dextran via clorosulphonic acid-pyridine complex (Nagasawa K. et al., Carbohydrate Research, 1972, 21: 420-423; Muhner C. et al., Carbohydrate Research 2001, 331: 203-208). Aspartic-dextran was prepared by aldehyde-dextran, previously generated via periodate oxidation (Fuentes M et al., Biotechnology Progress, 2004, 20, 284-288).

The ionic adsorption of the poly-blocker, just as the ionic adsorption of proteins, depends on the pH value at which the adsorption process occurs. In some cases in which the amino-coated surfaces of the arrays are blocked with sulfate-dextran (or another poly-anion), the poly-blocker treatment can be between pH 7-7.5.

In one embodiment, the array surface is positively charged, and sulfate-dextran is used as the poly-blocker.

The poly-blocker concentration can also be varied. An exemplary concentration of sulfate-dextran (in a solution that is applied to the surface) that effectively reduces non-specific binding to the surface is between 0.1 to 10 mg/mL, e.g., about 0.1 to 1 mg/mL or 1 to 5 mg/ml. For example, in some embodiments, high concentrations of poly-blocker are avoided as additional poly-blocker could increase surface charge and hence increase ionic adsorption of biomolecules to the surface.

Polymer size can influence the amount of ionic groups per molecule of the poly-blocker and can also influence the topography of the surface. Large poly-blockers can cover larger areas but can also generate poly-blocker brushes, rather than monolayers.

EXAMPLE

| 1 Protocol: Array printing |
| --- |
| 2 Material/Equipment |

Plasmid DNA
Psoralen-biotin (Pierce 29986)
Sodium acetate (3M, pH 5.5)
Isopropanol
Ethanol
UV Crosslinker, 365 nm wavelength (UVP 95-0228-01)
384 well plate for arraying, Genetix x7020
Polyclonal anti-GST antibody (GE Healthcare/Amersham 27457701)
Streptavidin (Cortex CE0301B)
BS[3] Linker (Pierce 21580)
Purified GST protein (Sigma G5663)
Whole mouse IgG antibody (Pierce 31204)
Centrifuge, Eppendorf 5810
QArray2
Silica packets (VWR 100489-246)
Genetix Bioassay dish dividers (x6026 divider only; x6027 with dish)
Corning deep bioassay dish (431111)
WellMate
Eppendorf Thermomixer 1) Prepare psoralen-biotin: Stock 10 mg/mL. Working solution 20 ng/μL. Add 10 μL of the working biotin solution to the 150 μL of DNA in the Greiner conical plate. A total of 200 ng of biotin should be added per sample. The Genmate may be used for this addition on a full plate basis.
2) Crosslink for 30 minutes with UV Crosslinker. Use max power set at 9999. The plates must be uncovered for this step. Total dose=8800 mJ/cm$^2$.
3) Add 20 μL of 3 M Sodium Acetate (pH 5.5). Add 120 μL of isopropanol. These two additions can be done with the Biomek FX. Cover the plate with an aluminum seal and mix by inverting 3 times.
4) Spin at 5300 rcf for 15 mins using the Sorvall RC12 centrifuge.
5) Discard the supernatant.
6) Add 100 μL of 80% ethanol to each well. The WellMate may be used for this addition.
7) Seal the plate with an aluminum seal and shake at 1000 rpm for ~2 mins on the Thermomixer.
8) Spin at 5300 rcf for 15 mins using the Sorvall RC12 centrifuge.
9) Discard the supernatant.
10) Dry the plate, uncovered, in the hood for 10 mins.

Array Sample Preparation:
1) Prepare master mix. For one 96-well plate prepare approximately 3 mL of master mix. Master mix contains polyclonal GST antibody (final: 1:100 dilution or 50 μg/mL), Streptavidin (final: 3.6 mg/mL) and BS[3] linker (final: 1.25 mg/mL or 2 mM).
e.g. 3 mL Master Mix:

| Streptavidin (66 mg/mL stock): | 166.5 μL |
| --- | --- |
| BS[3] Linker (50 mg/mL stock): | 75.0 μL |
| Polyclonal α-GST (5 mg/mL stock): | 30.0 μL |
| AC MQ H$_2$O: | 2728.5 μL |

2) For robotic master mix addition, aliquot the master mix evenly into each well of a PCR plate. Each well should contain enough master mix for the number of plates receiving master mix (i.e. 20 μL×number of plates) plus a 10 μL excess. For example, to add 20 μL master mix to 4 DNA pellet plates, each well of the master mix PCR plate should contain (4×20 μL)+10 μL=90 μL. This step is not necessary for manual master mix addition.
3) Add 20 μL to each well of the dry DNA pellet plates using the Biomek FX or a multi-channel pipette. Spin the plates down briefly and shake the plates rapidly at 1400 rpm for ~5 mins at room temperature on the Thermomixer. Briefly spin the plates down again.
4) Transfer 18 μL to 384 array plate. This transfer can be done using the Biomek FX or a multi-channel pipette.
5) Spin the plate down briefly.
6) Array, using the appropriate array setup and humidity control between 60%.
7) Put barcode labels on the bottom (non-arrayed) side of each slide. Maintain the slides order on the deck in numerical order.
8) Place the spotted slides, in order, on bioassay dishes with dividers. Each dish should accommodate approximately 15 slides. Fill the bottom of each bioassay dish with water so that only the bottom of the dish is covered. Do not use too much water and do not spill water onto the arrayed slides. Cover each dish and carefully stack the dishes together on top of a cart. Cover the entire stack with a sheet of aluminum foil on top. Wheel the slides into the cold room for over-night incubation.
9) Dry the slides and store at room temperature in a metal rack in a Lock-n-Lock box with a silica packet.

Protocol: Expression of the NAPPA Slides

| Material/Equipment | Amount (for 3 slides) |
| --- | --- |
| HybriWell gaskets (Grace HBW2160-1LA) | 3 |
| Cell free expression system i.e. rabbit reticulocyte lysate (Promega L4610) | 1 tube |
| RNaseOUT (Invitrogen 10777-019) | 8 μL |
| DEPC water (Ambion 9906) | 160 μL |
| SuperBlock (Pierce 37535) | ~30 mL |
| Blocking solution: 5% Milk in PBS with 0.2% Tween20 | ~120 mL |
| PBS | |
| Programmable chilling incubator, with leveling shelves | |
| Rocking shaker | |
| Genetix Bioassay dish dividers (x6026 divider only; x6027 with dish) | |
| Corning deep bioassay dish (431111) | |

1 Blocking: ~1 hr on rocking shaker at room temperature or 4° C. overnight in the cold room with SuperBlock or milk. Use ~30 mL in a pipette box for 4 slides.
2 Rinse with Milli-Q water. Dry with filtered compressed air.
3 Apply HybriWell gasket to each slide. Use the wooden stick to rub the areas where the adhesive is to make sure it is well stuck to the slide all around.
4 Pre-heat the incubator to be used for IVT at 30° C.
5 Prepare IVT. Each slide will require 130 μL of IVT lysate mix. Each tube after component addition will contain 400 μL of lysate mix. Since the lysate tubes cannot be re-frozen, always try to express slides in batches of some multiple of three.
e.g. 1 tube =3 slides =400 μL
16 μL TNT buffer
8 μL T7 polymerase 4 μL of -Met
  4 μL of -Leu or -Cys
  8 μL of RNaseOUT
  160 μL of DEPC water
  200 μL of reticulocyte lysate
6 Add IVT mix from the non-label or non-specimen end. Pipette the mix in slowly; Gently massage the HybriWell to spread the IVT mix over the array. Apply the small round port seals to both ports.
7 Place the slides on a bioassay dish with divider on top of the leveling shelf inside the incubator. Incubate for 1.5 hr at 30° C. for protein expression (e.g., between 29-31° C. or 28-32° C.), followed by 30 min at 15° C. for the query protein to bind to the immobilized protein.
8 Remove the HybriWell and immerse each slide in milk immediately; wash with milk three times, 3 minutes each, in a pipette box. Use about 30 mL milk per wash.
9 Block with milk on rocking shaker overnight at 4° C. or at room temperature for 1 hr.

Protocol: Detection of the NAPPA Arrays

| Material/Equipment | Amount (for 1 slide) |
|---|---|
| Primary AB, mouse anti-GST (Cell Signal 2624) | 150 μL of stock solution |
| Primary AB, mouse anti-HA | 150 μL of stock solution |
| Secondary AB, HRP-conjugated anti-mouse (Amersham NA931) | 150 μL of stock solution |
| TSA reagent (PerkinElmer SAT704B001EA) | 150 μL of stock solution |
| Milk (5% Milk in PBS with 0.2% Tween20) | 90 mL for 4 slides at once |
| PBS (pH 7.4) | 90 mL for 4 slides at once |
| Coverslips, 24 × 60 mm (VWR 48393-106) | 3 |
| Lifterslips, 24 × 65 mm (Erie 25X65I-2-5251-001-LS) | 3 |
| Pipette boxes | 1 |
| Scanner, PerkinElmer ProScanArray ™ | |

1) If needed, prepare antibody solutions in SuperBlock: 1:200 mGST, 1:1000 HA, 1:200 anti-mouse, 1:500 anti-human IgG. Store at 4° C.

2) If needed, prepare the TSA stock solution: add ~1 mL of Amplification Diluent (from TSA kit) to each of the 5 tubes with dried TSA. Vortex. Solution will turn bright pink. Pour those 5 solutions back into the diluent bottle. Take another ~1 mL of that mix for each tube, vortex again, and add back to the diluent bottle. Keep this solution at 4° C.

3) Apply primary AB (mouse anti-GST or mouse anti-HA) by adding 150 μL to the non-label or non-specimen end of the slide, then apply a coverslip. Generally, avoid drying the slides during this step. Incubate for 1 hr at RT; wash with milk on a rocking shaker (3 times, ~5 min each). Drain.

4) Apply secondary AB (anti-mouse HRP) by adding 150 □L to the non-label or non-specimen end of the slide, place a coverslip. Again, treat each slide one at a time starting with removal from the blocking milk through coverslip application. Generally, avoid drying the slides during this step. Incubate for 1 hr at RT; wash with PBS (pH 7.4) 3 times, ~5 min each. Quickly rinse with Milli-Q water. Drain.

5) Apply 150 □L TSA mix and place coverslip. Incubate for 10 minutes. Rinse in Milli-Q water; dry with filtered compressed air.

6) Scan.

EXAMPLE

Epoxy-Silane Coating 300 ml of 2% of epoxy silane(3-glycidyloxypropyl)triethoxysilane solution in acetone was prepared. The slides were treated with epoxy silane coating solution for 15 minutes at room temperature. The slides were rinsed with acetone and dried. The slides were stored at 4° C.

EXAMPLE

Aldehyde-Silane Coating

The aldehyde-groups were obtained from epoxy-activated slides described above. The epoxy group could be broken at acid pH or basic pH. The rupture of the oxirane ring resulted in a diol that was able to oxidize to aldehyde groups.

Use of Acidic pH

The epoxy-activated slides were incubated with a solution of sulfuric acid at pH 2 for 1 hour at room temperature. Next, the slides were rinsed with water and incubated with 100 mM sodium periodate solution for 2 hours at room temperature. The slides were then rinsed with water and dried. The slides were stored at 4° C.

Use of Basic pH

The epoxy-activated slides were incubated with a solution of sodium hydroxide at pH 12 for 1 hour at room temperature. Next, the slides were rinsed with water and incubated with 100 mM sodium periodate solution for 2 hours at room temperature. The slides were then rinsed with water and dried. The slides were stored at 4° C.

EXAMPLE

Elispot Assay

An Elispot Spot assay is used to detect T-cell responses by exposing the T-cell to a specific antigen and monitoring the response. A common response is the release of Interferon gamma (IFN-γ).

An Elispot-NAPPA array can be used to simultaneously detect T-cell responses to many antigens. A T-cell response to a specific antigen on the array can be captured by attaching an appropriate capture agent to a surface of the array such that the capture agent detects (e.g., binds) to the response signal. The array is contacted with T cells. The release of IFN-γ by the T-cell can be detected by affixing an anti-IFN-γ antibody onto the array surface.

EXAMPLE

Preparing Self-Assembled Monolayer on a Gold Surface

Different thiols (aliphatic thiols and PEG-thiols) are suspended in an ethanol solution to obtain a concentration of 100 mM. This is a stock solution, which is diluted with ethanol to obtain a coating solution with a concentration of 1 mM. Each slide has a capacity for 300 μL. 200 μL of the 1 mM solution is added to the slide, and a coverslide added fast (to prevent ethanol from evaporating). The slides are incubated overnight. Next, the slides are rinsed with ethanol and dried with an air can.

Other embodiments are within the scope of the following claims:

What is claimed:

1. A method comprising:
providing a substrate that comprises (i) a nucleic acid encoding a hybrid amino acid sequence comprising a test amino acid sequence and an affinity tag, and (ii) a binding agent that recognizes the affinity tag, wherein the nucleic acid is selectively bound to the substrate, and wherein the substrate is maintained under conditions permissive for the nucleic acid to be selectively bound to the substrate;
contacting the substrate with a translation effector to thereby translate the nucleic acid encoding the hybrid amino acid sequence;
maintaining the substrate under conditions permissive for the hybrid amino acid sequence to bind the binding agent; and
modifying substrate conditions such that the nucleic acid is removed from the substrate.

2. The method of claim 1 wherein the nucleic acid comprises DNA.

3. The method of claim 1 wherein the nucleic acid is selectively bound to the substrate by a reagent whose affinity for the nucleic acid varies with buffer conditions.

4. The method of claim 3 wherein the reagent binds the nucleic acid at a pH of less than 7.5, but releases the nucleic acid at a pH greater than 8.

5. The method of claim 3, wherein the reagent is $NH_2$—$[CH_2]_n$-$NH_3^+$ and n is between 2 and 5.

6. The method of claim 3, wherein the reagent is $NH_2$—$[CH_2]_n$-$NH_3^+$.

7. The method of claim 3, wherein the reagent is mono-amino-N-aminoethyl (MANAE).

8. A method comprising:
providing a substrate that comprises a multifunctional surface having a homo-functional group capable of reacting with proteins;
disposing, at a plurality of positionally distinguishable locations on the reactive multifunctional surface, (i) a nucleic acid encoding a hybrid amino acid sequence comprising a test amino acid sequence and an affinity tag, and (ii) a binding agent that recognizes the affinity tag, wherein the binding agent reacts with the reactive multifunctional surface and becomes covalently attached to the surface, and wherein the nucleic acid is selectively bound to the surface, wherein the surface is maintained under conditions permissive for the nucleic acid to be selectively bound to the surface; and
modifying substrate conditions such that the nucleic acid is removed from the substrate.

9. The method of claim 8 further comprising inactivating the reactive surface and contacting the substrate with a translation effector to thereby translate the hybrid amino acid sequence at each of the locations; and maintaining the substrate under conditions permissive for the hybrid amino acid sequence to bind the binding agent.

10. The method of claim 8, wherein at each location, the nucleic acid and the binding agent are disposed onto the substrate together.

11. The method of claim 8, wherein at each location, the nucleic acid and the binding agent are disposed onto the substrate separately.

12. The method of claim 8, wherein the homo-functional group is a primary amino group, an aldehyde group, an epoxy group, or a carboxyl group.

13. The method of claim 8, wherein said multifunctional surface comprises at least one multifunctional surface binding agent.

14. The method of claim 13, wherein said at least one multifunctional surface binding agent comprises a functional group to non-covalently bind a biomolecule.

15. The method of claim 13, wherein said at least one multifunctional surface binding agent comprises a functional group to covalently bind a biomolecule.

16. The method of claim 13, wherein said at least one multifunctional surface binding agent comprises a functional group to non-covalently bind a biomolecule and a functional group to covalently bind a biomolecule.

17. The method of claim 13, wherein said at least one multifunctional surface binding agent is selected from the group consisting of an epoxy-amino group, an amino-epoxy group, an epoxy-iminodiacetic acid group, and an epoxy-boronate group, or any combination thereof.

18. The method of claim 13, wherein said at least one multifunctional surface binding agent is a diamine group.

19. The method of claim 13, wherein said at least one multifunctional surface binding agent is a carboxyl group.

20. The method of claim 8, wherein said multifunctional surface comprises a polypeptide and at least one multifunctional surface binding agent.

21. The method of claim 20, wherein said polypeptide is a DNA binding polypeptide.

22. The method of claim 8, wherein said multifunctional surface comprises an antibody and at least one multifunctional surface binding agent.

23. A method comprising:
providing a substrate that comprises (i) a nucleic acid encoding a hybrid amino acid sequence comprising a test amino acid sequence and an affinity tag, and (ii) a binding agent that recognizes the affinity tag, wherein the substrate is maintained under conditions permissive for the nucleic acid to be bound to the substrate;
contacting the substrate with a translation effector to thereby translate the nucleic acid encoding the hybrid amino acid sequence;
maintaining the substrate under conditions permissive for the hybrid amino acid sequence to bind the binding agent; and
modifying substrate conditions such that the nucleic acid is removed from the substrate, but wherein the binding of the hybrid amino acid sequence to the binding agent is not substantially affected.

24. The method of claim 23, wherein the nucleic acid is selectively bound to the substrate.

25. The method of claim 23, wherein the pH of the buffer conditions varies.

26. The method of claim 24, wherein the nucleic acid is selectively bound by a reagent whose affinity for the nucleic acid varies.

27. The method of claim 25, wherein affinity of the reagent for the nucleic acid varies according to pH.

28. The method of claim 27, wherein the reagent binds the nucleic acid at a pH of less than 7.5, but releases the nucleic acid at a pH greater than 8.

29. The method of claim 23, wherein the modifying comprises treatment of the substrate with an enzyme.

30. The method of claim 29, wherein the enzyme comprises DNase.

31. The method of claim 29, wherein the enzyme comprises RNase.

32. The method of claim 23, wherein the substrate comprises a multifunctional surface.

33. The method of claim 32, wherein the multifunctional surface comprises at least one multifunctional surface binding agent.

34. The method of claim 33, wherein the at least one multifunctional surface binding agent comprises a diamine.

35. The method of claim 23, wherein the nucleic acid comprises DNA.

36. The method of claim 23, wherein the nucleic acid comprises RNA.

37. The method of claim 23, wherein the nucleic acid comprises mRNA.

38. The method of claim 1, wherein the interaction between the hybrid amino acid sequence and the binding agent is not substantially affected by the modifying.

39. The method of claim 1, wherein the modifying comprises reducing affinity of the substrate for the nucleic acid.

40. The method of claim 1, wherein the nucleic acid comprises RNA.

41. The method of claim 1, wherein the nucleic acid comprises mRNA.

42. The method of claim 3, wherein the pH of the buffer conditions varies.

43. The method of claim 1, wherein the nucleic acid is selectively removed.

* * * * *

UNITED STATES PATENT AND TRADEMARK OFFICE
CERTIFICATE OF CORRECTION

| | | |
|---|---|---|
| PATENT NO. | : 8,178,316 B2 | Page 1 of 1 |
| APPLICATION NO. | : 11/770111 | |
| DATED | : May 15, 2012 | |
| INVENTOR(S) | : Joshua LaBaer et al. | |

It is certified that error appears in the above-identified patent and that said Letters Patent is hereby corrected as shown below:

Title page, item 75, line 1:
 delete "Matfield" and replace with --Medfield--.

Signed and Sealed this
Tenth Day of July, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,178,316 B2 | Page 1 of 1 |
| APPLICATION NO. | : 11/770111 | |
| DATED | : May 15, 2012 | |
| INVENTOR(S) | : Labaer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 471 days.

Signed and Sealed this
Twenty-eighth Day of August, 2012

David J. Kappos
*Director of the United States Patent and Trademark Office*

UNITED STATES PATENT AND TRADEMARK OFFICE
CERTIFICATE OF CORRECTION

PATENT NO. : 8,178,316 B2
APPLICATION NO. : 11/770111
DATED : May 15, 2012
INVENTOR(S) : Labaer et al.

Page 1 of 1

It is certified that error appears in the above-identified patent and that said Letters Patent is hereby corrected as shown below:

In the Specification

Delete the paragraph beginning at Column 1, Line number 18 and replace it with the following paragraph:
This invention was made with government support under CA117374 and CA099191 awarded by the National Institutes of Health. The government has certain rights in the invention.

Signed and Sealed this
Second Day of September, 2025

Coke Morgan Stewart
*Acting Director of the United States Patent and Trademark Office*